(12) United States Patent
Cohen et al.

(10) Patent No.: US 10,398,435 B1
(45) Date of Patent: *Sep. 3, 2019

(54) RELEASABLE TISSUE ANCHORING DEVICE AND METHOD FOR USING

(71) Applicant: Microfabrica Inc., Van Nuys, CA (US)

(72) Inventors: Adam L. Cohen, Dallas, TX (US); Christopher R. Folk, Los Angeles, CA (US)

(73) Assignee: Microfabrica Inc., Van Nuys, CA (US)

( * ) Notice: Subject to any disclaimer, the term of this patent is extended or adjusted under 35 U.S.C. 154(b) by 406 days.

This patent is subject to a terminal disclaimer.

(21) Appl. No.: 15/019,927

(22) Filed: Feb. 9, 2016

Related U.S. Application Data

(63) Continuation of application No. 13/714,179, filed on Dec. 13, 2012, now Pat. No. 9,282,964, which is a
(Continued)

(51) Int. Cl.
*A61B 17/08* (2006.01)
*A61B 17/10* (2006.01)
*A61B 17/00* (2006.01)

(52) U.S. Cl.
CPC ........ *A61B 17/08* (2013.01); *A61B 17/00234* (2013.01); *A61B 17/083* (2013.01);
(Continued)

(58) Field of Classification Search
CPC ....... A61B 17/08; A61B 17/10; A61B 17/083; A61B 17/0057; A61B 2017/081;
(Continued)

(56) References Cited

U.S. PATENT DOCUMENTS 2,077,804 A 4/1937 Monroe et al.
2,132,264 A 10/1938 James et al.
(Continued)

OTHER PUBLICATIONS

Cohen, et al., "EFAB: Batch Production of Functional, Fully-Dense Metal Parts with Micron-Scale Features", Proc. 9th Solid Freeform Fabrication, The University of Texas at Austin, Aug. 1998, pp. 161-168.
(Continued)

*Primary Examiner* — Christopher L Templeton
(74) *Attorney, Agent, or Firm* — Dennis R. Smalley

(57) ABSTRACT

Embodiments of invention are directed to tissue approximation instruments that may be delivered to the body of a patient during minimally invasive or other surgical procedures. In one group of embodiments, the instrument has an elongated configuration with two sets of expandable wings that each have spreadable wings that can be made to expand when located on opposite sides of a distal tissue region and a proximal tissue region and can then be made to move toward one another to bring the two tissue regions into a more proximate position. The instrument is delivered through a needle or catheter and is controlled by relative movement of a push tube and control wire wherein the control wire can be released from the instrument via rotation in a first direction and can cause release of the approximation device from tissue that it is holding by rotation in the opposite direction.

7 Claims, 14 Drawing Sheets

Related U.S. Application Data continuation of application No. 12/651,388, filed on Dec. 31, 2009, now Pat. No. 8,454,652, which is a continuation-in-part of application No. 12/346,034, filed on Dec. 30, 2008, now abandoned, which is a continuation-in-part of application No. 11/591,911, filed on Nov. 1, 2006, now abandoned, and a continuation-in-part of application No. 11/598,968, filed on Nov. 14, 2006, now abandoned, and a continuation-in-part of application No. 11/625,807, filed on Jan. 22, 2007, now abandoned, said application No. 11/598,968 is a continuation-in-part of application No. 11/591,911, filed on Nov. 1, 2006, said application No. 11/625,807 is a continuation-in-part of application No. 11/598,968, filed on Nov. 14, 2006, and a continuation-in-part of application No. 11/582,049, filed on Oct. 16, 2006, now Pat. No. 7,686,770, and a continuation-in-part of application No. 11/444,999, filed on May 31, 2006, now abandoned, and a continuation-in-part of application No. 10/697,598, filed on Oct. 29, 2003, now abandoned, which is a continuation-in-part of application No. 10/697,598, filed on Oct. 29, 2003, said application No. 11/444,999 is a continuation-in-part of application No. 10/697,598, filed on Oct. 29, 2003, now abandoned.

(60) Provisional application No. 61/142,149, filed on Dec. 31, 2008, provisional application No. 61/018,269, filed on Dec. 31, 2007, provisional application No. 60/761,401, filed on Jan. 20, 2006, provisional application No. 60/736,961, filed on Nov. 14, 2005, provisional application No. 60/732,413, filed on Nov. 1, 2005, provisional application No. 60/726,794, filed on Oct. 14, 2005, provisional application No. 60/686,496, filed on May 31, 2005, provisional application No. 60/422,007, filed on Oct. 29, 2002.

(52) U.S. Cl.
CPC ..... *A61B 17/10* (2013.01); *A61B 2017/00526* (2013.01); *A61B 2017/081* (2013.01); *A61B 2017/088* (2013.01)

(58) Field of Classification Search
CPC ...... A61B 2017/088; A61B 2017/1103; A61B 2017/00606; A61B 2017/00588; A61B 2017/00619; A61B 2017/00632; A61B 2017/00637; A61B 2017/00641
See application file for complete search history.

(56) References Cited

U.S. PATENT DOCUMENTS

| | | |
|---|---|---|
| 2,398,220 A | 4/1946 | Gelpcke et al. |
| 3,874,388 A | 4/1975 | King et al. |
| 4,007,743 A | 2/1977 | Blake |
| 4,286,497 A | 9/1981 | Shamah |
| 4,519,100 A | 5/1985 | Wills et al. |
| 4,615,514 A | 10/1986 | Hamlin |
| 4,632,101 A | 12/1986 | Freedland |
| 4,721,103 A | 1/1988 | Freedland |
| 4,883,398 A | 11/1989 | Duncan |
| 4,890,613 A | 1/1990 | Golden et al. |
| 5,098,433 A | 3/1992 | Freedland |
| 5,190,637 A | 3/1993 | Guckel |
| 5,342,393 A | 8/1994 | Stack |
| 5,350,399 A | 9/1994 | Erlebacher et al. |
| 5,797,960 A | 8/1998 | Stevens et al. |
| 6,027,630 A | 2/2000 | Cohen |
| 6,051,007 A | 4/2000 | Hogendijk et al. |
| 6,406,420 B1 | 6/2002 | McCarthy et al. |
| 6,451,054 B1 | 9/2002 | Stevens |
| 6,461,365 B2 | 10/2002 | Bolduc et al. |
| 6,485,493 B1 | 11/2002 | Bremer |
| 6,699,263 B2 | 3/2004 | Cope |
| 6,790,377 B1 | 9/2004 | Cohen |
| 6,860,895 B1 | 3/2005 | Akerfeldt et al. |
| 6,913,607 B2 | 7/2005 | Ainsworth et al. |
| 6,913,614 B2 | 7/2005 | Marino et al. |
| 7,087,066 B2 | 8/2006 | Bolduc et al. |
| 7,097,650 B2 | 8/2006 | Weller et al. |
| 7,109,118 B2 | 9/2006 | Cohen et al. |
| 7,160,429 B2 | 1/2007 | Cohen et al. |
| 7,195,989 B2 | 3/2007 | Lockard et al. |
| 7,198,704 B2 | 4/2007 | Cohen et al. |
| 7,220,265 B2 | 5/2007 | Chanduszko et al. |
| 7,229,542 B2 | 6/2007 | Bang |
| 7,235,090 B2 | 6/2007 | Buckman et al. |
| 7,235,166 B2 | 6/2007 | Cohen et al. |
| 7,239,219 B2 | 7/2007 | Brown et al. |
| 7,252,861 B2 | 8/2007 | Smalley |
| 7,288,178 B2 | 10/2007 | Cohen et al. |
| 7,291,254 B2 | 11/2007 | Cohen et al. |
| 7,311,720 B2 | 12/2007 | Mueller et al. |
| 7,318,833 B2 | 1/2008 | Chanduszko |
| 7,368,044 B2 | 5/2008 | Cohen et al. |
| 7,431,729 B2 | 10/2008 | Chanduszko |
| 7,442,201 B2 | 10/2008 | Pugsley et al. |
| 7,498,714 B2 | 3/2009 | Lockard et al. |
| 7,501,328 B2 | 3/2009 | Lockard et al. |
| 7,611,616 B2 | 11/2009 | Cohen et al. |
| 7,686,770 B2 | 3/2010 | Cohen |
| 7,736,378 B2 | 6/2010 | Maahs et al. |
| 7,798,953 B1* | 9/2010 | Wilk ................. A61B 17/0057 600/16 |
| 2003/0221968 A1 | 12/2003 | Cohen et al. |
| 2004/0000489 A1 | 1/2004 | Zhang et al. |
| 2004/0004001 A1 | 1/2004 | Cohen et al. |
| 2004/0065550 A1 | 4/2004 | Zhang |
| 2004/0065555 A1 | 4/2004 | Zhang |
| 2004/0073219 A1 | 4/2004 | Skiba et al. |
| 2004/0122456 A1 | 6/2004 | Saadat et al. |
| 2004/0133236 A1 | 7/2004 | Chanduszko |
| 2004/0134772 A1 | 7/2004 | Cohen et al. |
| 2004/0146650 A1 | 7/2004 | Lockard et al. |
| 2004/0225324 A1 | 11/2004 | Marino et al. |
| 2005/0029109 A1 | 2/2005 | Zhang et al. |
| 2005/0067292 A1 | 3/2005 | Thompson et al. |
| 2005/0072681 A1 | 4/2005 | Cohen et al. |
| 2005/0230261 A1 | 10/2005 | Cohen et al. |
| 2005/0251205 A1 | 11/2005 | Ewers et al. |
| 2006/0282065 A1 | 12/2006 | Cohen |
| 2007/0112338 A1* | 5/2007 | Cohen ................. A61B 17/0401 606/1 |
| 2007/0158200 A1 | 7/2007 | Cohen et al. |
| 2007/0179527 A1* | 8/2007 | Eskuri ................ A61B 17/0057 606/213 |
| 2007/0198038 A1 | 8/2007 | Cohen et al. |
| 2007/0219459 A1 | 9/2007 | Cohen |
| 2007/0244517 A1 | 10/2007 | Callaghan |
| 2007/0250115 A1 | 10/2007 | Opolski et al. |
| 2007/0265648 A1 | 11/2007 | Cohen |
| 2008/0050524 A1 | 2/2008 | Kumar et al. |
| 2008/0243182 A1* | 10/2008 | Bates ................. A61B 17/0057 606/213 |
| 2009/0312789 A1 | 12/2009 | Kassab et al. |

OTHER PUBLICATIONS

Adam L. Cohen, et al., "EFAB: Rapid, Low-Cost Desktop Micromachining of High Aspect Ratio True 3-D MEMS", Proc. 12th IEEE Micro Electro Mechanical Systems Workshop, IEEE, Jan. 17-21, 1999, pp. 244-251.

"Microfabrication—Rapid Prototyping's Killer Applications", Rapid Prototyping Report, CAD/CAM Publishing, Inc., Jun. 1999, pp. 1-5.

Adam L. Cohen, "3-D Micromachining by Electrochemical Fabrication", Micromachine Devices, Mar. 1999, pp. 6-7.

(56) References Cited

OTHER PUBLICATIONS

Gang Zhang, et al., "EFAB: Rapid Desktop Manufacturing of True 3-D Microstructures", Proc. 2nd International Conference on Integrated MicroNanotechnology for Space Applications, The Aerospace Co., Apr. 1999.

F. Tseng, et al., "EFAB: High Aspect Ratio, Arbitrary 3-D Metal Microstructures Using a Low-Cost Automated Batch Process", 3rd International Workshop on High Aspect Ratio Microstructure Technology (HARMST'99), Jun. 1999.

Adam L. Cohen, et al., "EFAB: Low-Cost, Automated Electrochemical Batch Fabrication of Arbitrary 3-D Microstructures", Micromachining and Microfabrication Process Technology, SPIE 1999 Symposium on Micromachining and Microfabrication, Sep. 1999.

F. Tseng, et al., "EFAB: High Aspect Ratio, Arbitrary 3-D Metal Microstructures Using a Low-Cost Automated Batch Process", MEMS Symposium, ASME 1999 International Mechanical Engineering Congress and Exposition, Nov. 1999, pp. 55-60.

Adam L. Cohen, "Electrochemical Fabrication (EFABTM)", Chapter 19 of the MEMS Handbook, edited by Mohamed Gad-El-Hak, CRC Press, 2002, pp. 19/1-19/23.

Hill, Dr. Steve, "An E-FAB Way for Making the Micro World", Materials World is the journal of the Institute of Materials, Sep. 1999, vol. 7, No. 9, pp. 538-539.

Nikolay V. Vasiiyev, et al., "Beating-Heart Pach Closure of Muscular Ventricular Septal Defects Under Real-Time Three Dimensional Echocardiographic Guidance: A Preclinical Study", J. Thorac, Cardiovas, Surg., 2008, pp. 603-609, vol. 153, No. 3, The American Association of Thoracic Surgery.

Nikolay V. Vasiiyev, et al., "Three Dimensional Echo and Videocardioscopy-Guided Atrial Septal Defect Closure", Ann. Thorac. Surg., 2006, pp. 1322-1326, vol. 82, The Society of Thoracic Surgeons.

\* cited by examiner

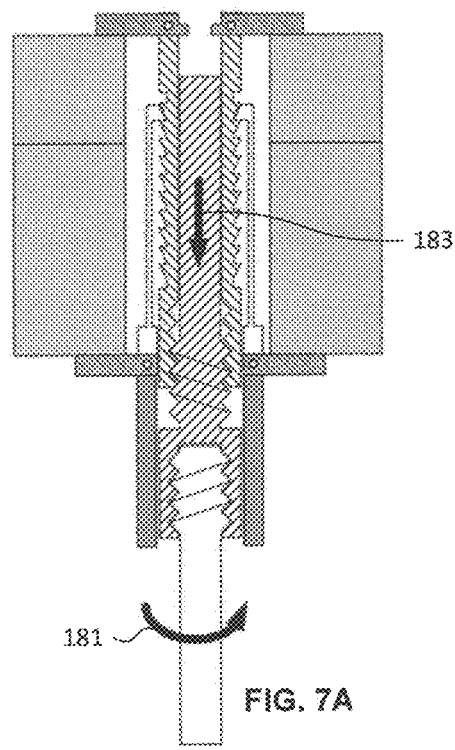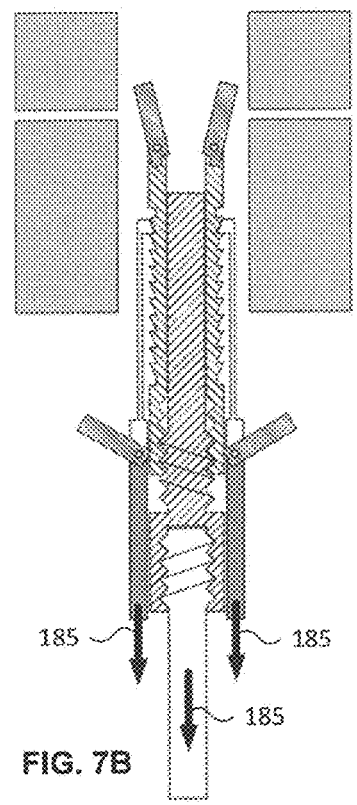
FIG. 7A
FIG. 7B

RELEASABLE TISSUE ANCHORING DEVICE AND METHOD FOR USING

U.S. GOVERNMENT RIGHTS

This was made with government support under Grant No. R01 HL087797 awarded by the National Institutes of Health. The Government has certain rights in the inventions.

RELATED APPLICATIONS

The below table sets forth the priority claims for the instant application along with filing dates, patent numbers, and issue dates as appropriate. Each of the listed applications is incorporated herein by reference as if set forth in full herein including any appendices attached thereto.

| application Ser. No. | Continuity Type | application Ser. No. | Which was Filed (YYYY-MM-DD) | Which is now | Which issued on |
|---|---|---|---|---|---|
| This application | is a CNT of | 13/714,179 | 2012-12-13 | pending | — |
| 13/714,179 | is a CNT of | 12/651,388 | 2009-12-31 | U.S. Pat. No. 8,454,652 | 2013 Jun. 4 |
| 12/651,388 | claims benefit of | 61/142,149 | 2008-12-31 | expired | — |
| 12/651,388 | is a CIP of | 12/346,034 | 2008-12-30 | abandoned | — |
| 12/346,034 | claims benefit of | 61/018,269 | 2007-12-31 | expired | — |
| 12/346,034 | is a CIP of | 11/591,911 | 2006-11-01 | abandoned | — |
| 12/346,034 | is a CIP of | 11/598,968 | 2006-11-14 | abandoned | — |
| 12/346,034 | is a CIP of | 11/625,807 | 2007-01-22 | abandoned | — |
| 11/591,911 | claims benefit of | 60/732,413 | 2005-11-01 | expired | — |
| 11/591,911 | claims benefit of | 60/736,961 | 2005-11-14 | expired | — |
| 11/591,911 | claims benefit of | 60/761,401 | 2006-01-20 | expired | — |
| 11/598,968 | claims benefit of | 60/736,961 | 2005-11-14 | expired | — |
| 11/598,968 | claims benefit of | 60/761,401 | 2006-01-20 | expired | — |
| 11/598,968 | is a CIP of | 11/591,911 | 2006-11-01 | abandoned | — |
| 11/625,807 | claims benefit of | 60/761,401 | 2006-01-20 | expired | — |
| 11/625,807 | is a CIP of | 11/598,968 | 2006-11-14 | abandoned | — |
| 11/625,807 | is a CIP of | 11/582,049 | 2006-10-16 | U.S. Pat. No. 7,686,770 | 2010 Mar. 30 |
| 11/625,807 | is a CIP of | 11/444,999 | 2006-05-31 | abandoned | — |
| 11/625,807 | is a CIP of | 10/697,598 | 2003-10-29 | abandoned | — |
| 11/582,049 | claims benefit of | 60/726,794 | 2005-10-14 | expired | — |
| 11/444,999 | claims benefit of | 60/686,496 | 2005-05-31 | expired | — |
| 11/444,999 | is a CIP of | 10/697,598 | 2003-10-29 | abandoned | — |
| 10/697,598 | claims benefit of | 60/422,007 | 2002-10-29 | expired | — |

FIELD OF THE INVENTION

The present invention relates to medical devices or instruments and in particular to medical devices that can be used for tissue approximation and retention/fixation that may be implemented in a surgical procedure (e.g. a minimally invasive surgical procedure). In some embodiments a microscale or millimeter scale working portion of the device or instrument may be formed using a multilayer, multi-material fabrication process.

BACKGROUND OF THE INVENTION

Electrochemical Fabrication:

An electrochemical fabrication technique for forming three-dimensional structures from a plurality of adhered layers is being commercially pursued by Microfabrica® Inc. (formerly MEMGen Corporation) of Van Nuys, Calif. under the name EFAB®.

Various electrochemical fabrication techniques were described in U.S. Pat. No. 6,027,630, issued on Feb. 22, 2000 to Adam Cohen. Some embodiments of this electrochemical fabrication technique allow the selective deposition of a material using a mask that includes a patterned conformable material on a support structure that is independent of the substrate onto which plating will occur. When desiring to perform an electrodeposition using the mask, the conformable portion of the mask is brought into contact with a substrate, but not adhered or bonded to the substrate, while in the presence of a plating solution such that the contact of the conformable portion of the mask to the substrate inhibits deposition at selected locations. For convenience, these masks might be generically called conformable contact masks; the masking technique may be generically called a conformable contact mask plating process. More specifically, in the terminology of Microfabrica Inc. such masks have come to be known as INSTANT MASKS™ and the process known as INSTANT MASKING™ or INSTANT MASK™ plating. Selective depositions using conformable contact mask plating may be used to form single selective deposits of material or may be used in a process to form multi-layer structures. The teachings of the '630 patent are hereby incorporated herein by reference as if set forth in full herein. Since the filing of the patent application that led to the above noted patent, various papers about conformable contact mask plating (i.e. INSTANT MASKING) and electrochemical fabrication have been published:

(1) A. Cohen, G. Zhang, F. Tseng, F. Mansfeld, U. Frodis and P. Will, "EFAB: Batch production of functional, fully-dense metal parts with micro-scale features", Proc. 9th Solid Freeform Fabrication, The University of Texas at Austin, p 161, August 1998.

(2) A. Cohen, G. Zhang, F. Tseng, F. Mansfeld, U. Frodis and P. Will, "EFAB: Rapid, Low-Cost Desktop Micromachining of High Aspect Ratio True 3-D MEMS", Proc. 12th IEEE Micro Electro Mechanical Systems Workshop, IEEE, p 244, January 1999.

(3) A. Cohen, "3-D Micromachining by Electrochemical Fabrication", Micromachine Devices, March 1999.

(4) G. Zhang, A. Cohen, U. Frodis, F. Tseng, F. Mansfeld, and P. Will, "EFAB: Rapid Desktop Manufacturing of True 3-D Microstructures", Proc. 2nd International Conference on Integrated MicroNanotechnology for Space Applications, The Aerospace Co., April 1999.

(5) F. Tseng, U. Frodis, G. Zhang, A. Cohen, F. Mansfeld, and P. Will, "EFAB: High Aspect Ratio, Arbitrary 3-D Metal Microstructures using a Low-Cost Automated Batch Process", 3rd International Workshop on High Aspect Ratio MicroStructure Technology (HARMST'99), June 1999.

(6) A. Cohen, U. Frodis, F. Tseng, G. Zhang, F. Mansfeld, and P. Will, "EFAB: Low-Cost, Automated Electrochemical Batch Fabrication of Arbitrary 3-D Microstructures", Micromachining and Microfabrication Process Technology, SPIE 1999 Symposium on Micromachining and Microfabrication, September 1999.

(7) F. Tseng, G. Zhang, U. Frodis, A. Cohen, F. Mansfeld, and P. Will, "EFAB: High Aspect Ratio, Arbitrary 3-D Metal Microstructures using a Low-Cost Automated Batch Process", MEMS Symposium, ASME 1999 International Mechanical Engineering Congress and Exposition, November, 1999.

(8) A. Cohen, "Electrochemical Fabrication (EFAB™)", Chapter 19 of The MEMS Handbook, edited by Mohamed Gad-El-Hak, CRC Press, 2002.

(9) Microfabrication—Rapid Prototyping's Killer Application", pages 1-5 of the Rapid Prototyping Report, CAD/CAM Publishing, Inc., June 1999.

The disclosures of these nine publications are hereby incorporated herein by reference as if set forth in full herein.

An electrochemical deposition for forming multilayer structures may be carried out in a number of different ways as set forth in the above patent and publications. In one form, this process involves the execution of three separate operations during the formation of each layer of the structure that is to be formed:

1. Selectively depositing at least one material by electrodeposition upon one or more desired regions of a substrate. Typically this material is either a structural material or a sacrificial material.

2. Then, blanket depositing at least one additional material by electrodeposition so that the additional deposit covers both the regions that were previously selectively deposited onto, and the regions of the substrate that did not receive any previously applied selective depositions. Typically this material is the other of a structural material or a sacrificial material.

3. Finally, planarizing the materials deposited during the first and second operations to produce a smoothed surface of a first layer of desired thickness having at least one region containing the at least one material and at least one region containing at least the one additional material.

After formation of the first layer, one or more additional layers may be formed adjacent to an immediately preceding layer and adhered to the smoothed surface of that preceding layer. These additional layers are formed by repeating the first through third operations one or more times wherein the formation of each subsequent layer treats the previously formed layers and the initial substrate as a new and thickening substrate.

Once the formation of all layers has been completed, at least a portion of at least one of the materials deposited is generally removed by an etching process to expose or release the three-dimensional structure that was intended to be formed. The removed material is a sacrificial material while the material that forms part of the desired structure is a structural material.

The preferred method of performing the selective electrodeposition involved in the first operation is by conformable contact mask plating. In this type of plating, one or more conformable contact (CC) masks are first formed. The CC masks include a support structure onto which a patterned conformable dielectric material is adhered or formed. The conformable material for each mask is shaped in accordance with a particular cross-section of material to be plated (the pattern of conformable material is complementary to the pattern of material to be deposited). At least one CC mask is used for each unique cross-sectional pattern that is to be plated.

The support for a CC mask is typically a plate-like structure formed of a metal that is to be selectively electroplated and from which material to be plated will be dissolved. In this typical approach, the support will act as an anode in an electroplating process. In an alternative approach, the support may instead be a porous or otherwise perforated material through which deposition material will pass during an electroplating operation on its way from a distal anode to a deposition surface. In either approach, it is possible for multiple CC masks to share a common support, i.e. the patterns of conformable dielectric material for plating multiple layers of material may be located in different areas of a single support structure. When a single support structure contains multiple plating patterns, the entire structure is referred to as the CC mask while the individual plating masks may be referred to as "submasks". In the present application such a distinction will be made only when relevant to a specific point being made.

In preparation for performing the selective deposition of the first operation, the conformable portion of the CC mask is placed in registration with and pressed against a selected portion of (1) the substrate, (2) a previously formed layer, or (3) a previously deposited portion of a layer on which deposition is to occur. The pressing together of the CC mask and relevant substrate occur in such a way that all openings, in the conformable portions of the CC mask contain plating solution. The conformable material of the CC mask that contacts the substrate acts as a barrier to electrodeposition while the openings in the CC mask that are filled with electroplating solution act as pathways for transferring material from an anode (e.g. the CC mask support) to the non-contacted portions of the substrate (which act as a cathode during the plating operation) when an appropriate potential and/or current are supplied.

An example of a CC mask and CC mask plating are shown in FIGS. 1A-1C. FIG. 1A shows a side view of a CC mask 8 consisting of a conformable or deformable (e.g. elastomeric) insulator 10 patterned on an anode 12. The anode has two functions. One is as a supporting material for the patterned insulator 10 to maintain its integrity and alignment since the pattern may be topologically complex (e.g., involving isolated "islands" of insulator material). The other function is as an anode for the electroplating operation. FIG. 1A also depicts a substrate 6, separated from mask 8, onto which material will be deposited during the process of forming a layer. CC mask plating selectively deposits material 22 onto substrate 6 by simply pressing the insulator against the substrate then electrodepositing material through apertures 26a and 26b in the insulator as shown in FIG. 1B. After deposition, the CC mask is separated, preferably non-destructively, from the substrate 6 as shown in FIG. 1C.

The CC mask plating process is distinct from a "through-mask" plating process in that in a through-mask plating process the separation of the masking material from the substrate would occur destructively. Furthermore in a through mask plating process, opening in the masking material are typically formed while the masking material is in contact with and adhered to the substrate. As with through-mask plating, CC mask plating deposits material selectively and simultaneously over the entire layer. The plated region may consist of one or more isolated plating regions where these isolated plating regions may belong to a single structure that is being formed or may belong to multiple structures that are being formed simultaneously. In CC mask plating as individual masks are not intentionally destroyed in the removal process, they may be usable in multiple plating operations.

Another example of a CC mask and CC mask plating is shown in FIGS. 1D-1G. FIG. 1D shows an anode 12' separated from a mask 8' that includes a patterned conformable material 10' and a support structure 20. FIG. 1D also depicts substrate 6 separated from the mask 8'. FIG. 1E illustrates the mask 8' being brought into contact with the substrate 6. FIG. 1F illustrates the deposit 22' that results from conducting a current from the anode 12' to the substrate 6. FIG. 1G illustrates the deposit 22' on substrate 6 after separation from mask 8'. In this example, an appropriate electrolyte is located between the substrate 6 and the anode 12' and a current of ions coming from one or both of the solution and the anode are conducted through the opening in the mask to the substrate where material is deposited. This type of mask may be referred to as an anodeless INSTANT MASK™ (AIM) or as an anodeless conformable contact (ACC) mask.

Unlike through-mask plating, CC mask plating allows CC masks to be formed completely separate from the substrate on which plating is to occur (e.g. separate from a three-dimensional (3D) structure that is being formed). CC masks may be formed in a variety of ways, for example, using a photolithographic process. All masks can be generated simultaneously, e.g. prior to structure fabrication rather than during it. This separation makes possible a simple, low-cost, automated, self-contained, and internally-clean "desktop factory" that can be installed almost anywhere to fabricate 3D structures, leaving any required clean room processes, such as photolithography to be performed by service bureaus or the like.

An example of the electrochemical fabrication process discussed above is illustrated in FIGS. 2A-2F. These figures show that the process involves deposition of a first material 2 which is a sacrificial material and a second material 4 which is a structural material. The CC mask 8, in this example, includes a patterned conformable material (e.g. an elastomeric dielectric material) 10 and a support 12 which is made from deposition material 2. The conformal portion of the CC mask is pressed against substrate 6 with a plating solution 14 located within the openings 16 in the conformable material 10. An electric current, from power supply 18, is then passed through the plating solution 14 via (a) support 12 which doubles as an anode and (b) substrate 6 which doubles as a cathode. FIG. 2A illustrates that the passing of current causes material 2 within the plating solution and material 2 from the anode 12 to be selectively transferred to and plated on the substrate 6. After electroplating the first deposition material 2 onto the substrate 6 using CC mask 8, the CC mask 8 is removed as shown in FIG. 2B. FIG. 2C depicts the second deposition material 4 as having been blanket-deposited (i.e. non-selectively deposited) over the previously deposited first deposition material 2 as well as over the other portions of the substrate 6. The blanket deposition occurs by electroplating from an anode (not shown), composed of the second material, through an appropriate plating solution (not shown), and to the cathode/substrate 6. The entire two-material layer is then planarized to achieve precise thickness and flatness as shown in FIG. 2D. After repetition of this process for all layers, the multi-layer structure 20 formed of the second material 4 (i.e. structural material) is embedded in first material 2 (i.e. sacrificial material) as shown in FIG. 2E. The embedded structure is etched to yield the desired device, i.e. structure 20, as shown in FIG. 2F.

Various components of an exemplary manual electrochemical fabrication system 32 are shown in FIGS. 3A-3C. The system 32 consists of several subsystems 34, 36, 38, and 40. The substrate holding subsystem 34 is depicted in the upper portions of each of FIGS. 3A-3C and includes several components: (1) a carrier 48, (2) a metal substrate 6 onto which the layers are deposited, and (3) a linear slide 42 capable of moving the substrate 6 up and down relative to the carrier 48 in response to drive force from actuator 44. Subsystem 34 also includes an indicator 46 for measuring differences in vertical position of the substrate which may be used in setting or determining layer thicknesses and/or deposition thicknesses. The subsystem 34 further includes feet 68 for carrier 48 which can be precisely mounted on subsystem 36.

The CC mask subsystem 36 shown in the lower portion of FIG. 3A includes several components: (1) a CC mask 8 that is actually made up of a number of CC masks (i.e. submasks) that share a common support/anode 12, (2) precision X-stage 54, (3) precision Y-stage 56, (4) frame 72 on which the feet 68 of subsystem 34 can mount, and (5) a tank 58 for containing the electrolyte 16. Subsystems 34 and 36 also include appropriate electrical connections (not shown) for connecting to an appropriate power source (not shown) for driving the CC masking process.

The blanket deposition subsystem 38 is shown in the lower portion of FIG. 3B and includes several components: (1) an anode 62, (2) an electrolyte tank 64 for holding plating solution 66, and (3) frame 74 on which feet 68 of subsystem 34 may sit. Subsystem 38 also includes appropriate electrical connections (not shown) for connecting the anode to an appropriate power supply (not shown) for driving the blanket deposition process.

The planarization subsystem 40 is shown in the lower portion of FIG. 3C and includes a lapping plate 52 and associated motion and control systems (not shown) for planarizing the depositions.

In addition to teaching the use of CC masks for electrodeposition purposes, the '630 patent also teaches that the CC masks may be placed against a substrate with the polarity of the voltage reversed and material may thereby be selectively removed from the substrate. It indicates that such removal processes can be used to selectively etch, engrave, and polish a substrate, e.g., a plaque.

The '630 patent further indicates that the electroplating methods and articles disclosed therein allow fabrication of devices from thin layers of materials such as, e.g., metals, polymers, ceramics, and semiconductor materials. It further indicates that although the electroplating embodiments described therein have been described with respect to the use of two metals, a variety of materials, e.g., polymers, ceramics and semiconductor materials, and any number of metals can be deposited either by the electroplating methods therein, or in separate processes that occur throughout the electroplating method. It indicates that a thin plating base can be deposited, e.g., by sputtering, over a deposit that is insufficiently conductive (e.g., an insulating layer) so as to enable subsequent electroplating. It also indicates that multiple support materials (i.e. sacrificial materials) can be included in the electroplated element allowing selective removal of the support materials.

The '630 patent additionally teaches that the electroplating methods disclosed therein can be used to manufacture elements having complex microstructure and close tolerances between parts. An example is given with the aid of FIGS. 14A-14E of that patent. In the example, elements having parts that fit with close tolerances, e.g., having gaps between about 1-5 um, including electroplating the parts of the device in an unassembled, preferably pre-aligned, state and once fabricated. In such embodiments, the individual parts can be moved into operational relation with each other or they can simply fall together. Once together the separate parts may be retained by clips or the like.

Another method for forming microstructures from electroplated metals (i.e. using electrochemical fabrication techniques) is taught in U.S. Pat. No. 5,190,637 to Henry Guckel, entitled "Formation of Microstructures by Multiple Level Deep X-ray Lithography with Sacrificial Metal layers". This patent teaches the formation of metal structure utilizing through mask exposures. A first layer of a primary metal is electroplated onto an exposed plating base to fill a void in a photoresist (the photoresist forming a through mask having a desired pattern of openings), the photoresist is then removed and a secondary metal is electroplated over the first layer and over the plating base. The exposed surface of the secondary metal is then machined down to a height which exposes the first metal to produce a flat uniform surface extending across both the primary and secondary metals. Formation of a second layer may then begin by applying a photoresist over the first layer and patterning it (i.e. to form a second through mask) and then repeating the process that was used to produce the first layer to produce a second layer of desired configuration. The process is repeated until the entire structure is formed and the secondary metal is removed by etching. The photoresist is formed over the plating base or previous layer by casting and patterning of the photoresist (i.e. voids formed in the photoresist) are formed by exposure of the photoresist through a patterned mask via X-rays or UV radiation and development of the exposed or unexposed areas.

The '637 patent teaches the locating of a plating base onto a substrate in preparation for electroplating materials onto the substrate. The plating base is indicated as typically involving the use of a sputtered film of an adhesive metal, such as chromium or titanium, and then a sputtered film of the metal that is to be plated. It is also taught that the plating base may be applied over an initial layer of sacrificial material (i.e. a layer or coating of a single material) on the substrate so that the structure and substrate may be detached if desired. In such cases after formation of the structure the sacrificial material forming part of each layer of the structure may be removed along the initial sacrificial layer to free the structure. Substrate materials mentioned in the '637 patent include silicon, glass, metals, and silicon with protected semiconductor devices. A specific example of a plating base includes about 150 angstroms of titanium and about 300 angstroms of nickel, both of which are sputtered at a temperature of 160° C. In another example it is indicated that the plating base may consist of 150 angstroms of titanium and 150 angstroms of nickel where both are applied by sputtering.

Electrochemical Fabrication provides the ability to form prototypes and commercial quantities of miniature objects, parts, structures, devices, and the like at reasonable costs and in reasonable times. In fact, Electrochemical Fabrication is an enabler for the formation of many structures that were hitherto impossible to produce. Electrochemical Fabrication opens the spectrum for new designs and products in many industrial fields. Even though Electrochemical Fabrication offers this new capability and it is understood that Electrochemical Fabrication techniques can be combined with designs and structures known within various fields to produce new structures, certain uses for Electrochemical Fabrication provide designs, structures, capabilities and/or features not known or obvious in view of the state of the art.

A need exists in various fields for miniature devices having improved characteristics, reduced fabrication times, reduced fabrication costs, simplified fabrication processes, greater versatility in device design, improved selection of materials, improved material properties, more cost effective and less risky production of such devices, and/or more independence between geometric configuration and the selected fabrication process.

SUMMARY OF THE INVENTION

It is an object of some embodiments of the invention to provide an improved tissue approximation device that is readily removable.

It is an object of some embodiments of the invention to provide an improved tissue approximation device that uses oppositely oriented thread elements to provide for release of a control wire and extraction of the device as a whole.

It is an object of some embodiments of the invention to provide a method for using the device of the first or second objects in the performance of a minimally invasive tissue approximation procedure.

Other objects and advantages of various embodiments of the invention will be apparent to those of skill in the art upon review of the teachings herein. The various embodiments of the invention, set forth explicitly herein or otherwise ascertained from the teachings herein, may address one or more of the above objects alone or in combination, or alternatively may address some other object ascertained from the teachings herein. It is not necessarily intended that all objects be addressed by any single aspect of the invention even though that may be the case with regard to some aspects.

A first aspect of the invention provides a medical instrument for approximating tissue within a patient's body during a minimally invasive surgical procedure, including: (a) a first set of expandable elements; (b) a second set of expandable elements; (c) a rail along which the first and second sets of expandable elements are located; and (d) a locking mechanism for allowing the first and second sets of expandable elements to be moved to a more proximate positions while inhibiting movement of the first and second sets of expandable elements to a more distant relative position along the length of the rail, after being moved to a more proximate position; (e) a threaded engagement feature for engaging a control wire; (f) a seat region for engaging a push tube wherein the wire and the push tube engage relatively movable elements and that upon relative motion can be made to bring the first and second set of expandable elements to their more proximate positions; (g) a controllable stop element that inhibits the distal expansion wings from extending beyond a desired retention position when located in a first position and allows distal axial collapse of the distal wings when located in another position so that the instrument may be extracted in its entirety from the proximal side of the tissue.

Numerous variations of the first aspect of the invention exist and include, for example, (1) the device wherein the control wire is rotatable relative to the engagement feature such that upon rotation in one direction the control wire is disengaged while rotation in the opposite direction causes the turning of an oppositely thread screw which causes the movement of the stop to the second position, (2) the medical instrument wherein at least one of the first set of expandable elements or the second set of expandable elements include toggle wings that pivot open along at least one axis that is perpendicular to a longitudinal axis of the instrument, and (3) the medical instrument wherein at least one of the first set of expandable elements or the second set of expandable elements include wings that expand by pivoting about at least one axis that is parallel to a longitudinal axis of the instrument and are actuated via a rotational motion of the instrument along its longitudinal axis.

Further variations of the second listed variation of the first aspect of the invention include, for example, (a) the medical instrument wherein the toggle wings expand via a force induced by at least one spring located within the instrument, and (b) the medical instrument wherein the other of the first set of expandable elements or the second set of expandable elements include toggle wings that pivot open along at least one axis that is perpendicular to a longitudinal axis of the instrument.

Yet further variations of the 2(b) listed variation of the first aspect of the invention include, for example, (i) the medical instrument wherein the toggle wings of the other of the first set of expandable elements or the second set of expandable elements expand via a force induced by at least one spring located within the instrument.

A second aspect of the invention provides a surgical procedure for approximating tissue within a patient's body, including: (a) locating an approximation instrument within the body of a patient at the end of a catheter; the instrument including: (i) a first set of expandable elements; (ii) a second set of expandable elements; (iii) a rail along which the first and second sets of expandable elements are located; and (iv) a locking mechanism for allowing the first and second sets of expandable elements to be moved to a more proximate positions while inhibiting movement of the first and second sets of expandable elements to a more distant relative position along the length of the rail, after being moved to a more proximate position; (v) a threaded engagement feature for engaging a control wire; (vi) a seat region for engaging a push tube wherein the wire and the push tube engage relatively movable elements and that upon relative motion can be made to bring the first and second set of expandable elements to their more proximate positions; (vii) a controllable stop element that inhibits the distal expansion wings from extending beyond a desired retention position when located in a first position and allows distal axial collapse of the distal wings when located in another position so that the instrument may be extracted in its entirety from the proximal side of the tissue; (b) inserting a distal end of the instrument through a proximal tissue region and then through a separated distal tissue region; (c) expanding the first set of expandable elements (d) locating the first set of expanded elements against a wall of the distal tissue region; (d) expanding the second set of expandable elements (e) locating the second set of expanded elements against a wall of the proximal tissue region; (e) relatively moving the first set of expanded elements and the second set of expanded elements toward one another to bring the proximal and distal tissue regions into a more proximate position; and (f) releasing at least a portion of the instrument from the catheter by rotating a portion of the instrument in a first direction via motion of the control wire so that the portion of instrument that contains the first and second sets of expanded elements remains in the body of the patient and retains the distal and proximal tissue regions in the more proximate position.

Numerous variations of the first aspect of the invention exist and include, for example, (1) the method wherein the instrument is disengaged from the distal and proximal tissue regions by rotating the a portion of the instrument in an opposite direction to that of the first direction to allow collapse of the distal wings in a distal direction as the instrument is extracted in a proximal direction.

The disclosure of the present invention provides for the fabrication of devices from a plurality of adhered layers wherein each successive layer includes at least two materials, one of which is a structural material and the other of which is a sacrificial material, and wherein each successive layer defines a successive cross-section of the three-dimensional structure, and wherein the forming of each of the plurality of successive layers includes: (i) depositing a first of the at least two materials, (ii) depositing a second of the at least two materials, (ii) planarizing the first and second materials; and after the forming of the plurality of successive layers, separating at least a portion of the sacrificial material from the structural material to reveal the three-dimensional structure.

Other aspects of the invention will be understood by those of skill in the art upon review of the teachings herein. Other aspects of the invention may involve combinations of the above noted aspects of the invention. These other aspects of the invention may provide various combinations of the aspects presented above as well as provide other configurations, structures, functional relationships, and processes that have not been specifically set forth above.

BRIEF DESCRIPTION OF THE DRAWINGS

FIGS. 7A-7B illustrate a process for releasing the device of FIG. 5 from tissue.

DETAILED DESCRIPTION OF PREFERRED EMBODIMENTS

Electrochemical Fabrication in General

FIGS. 1A-1G, 2A-2F, and 3A-3C illustrate various features of one form of electrochemical fabrication. Other electrochemical fabrication techniques are set forth in the '630 patent referenced above, in the various previously incorporated publications, in various other patents and patent applications incorporated herein by reference. Still others may be derived from combinations of various approaches described in these publications, patents, and applications, or are otherwise known or ascertainable by those of skill in the art from the teachings set forth herein. All of these techniques may be combined with those of the various embodiments of various aspects of the invention to yield enhanced embodiments. Still other embodiments may be derived from combinations of the various embodiments explicitly set forth herein.

Figure 1A:
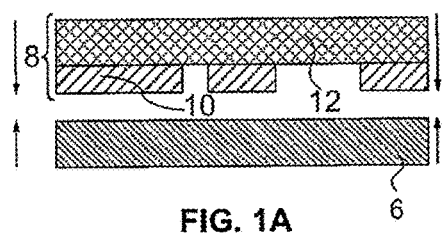
FIGS. 1A-1C schematically depict side views of various stages of a CC mask plating process, while FIGS. 1D-G schematically depict a side views of various stages of a CC mask plating process using a different type of CC mask.
Figure 1B:
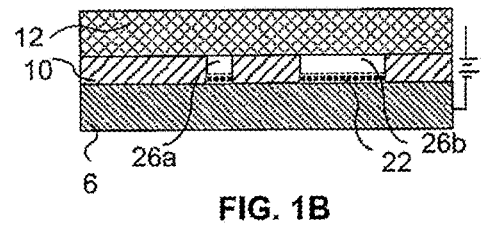
Figure 1C:
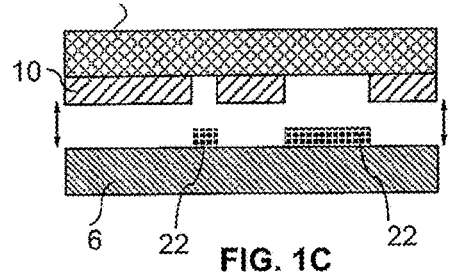
Figure 1D:
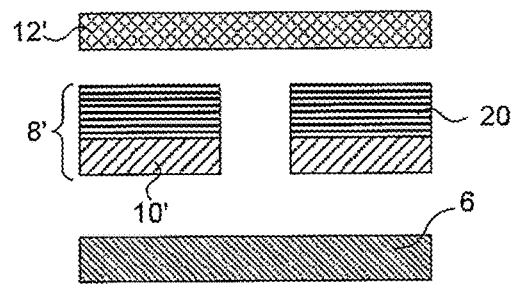
Figure 1E:
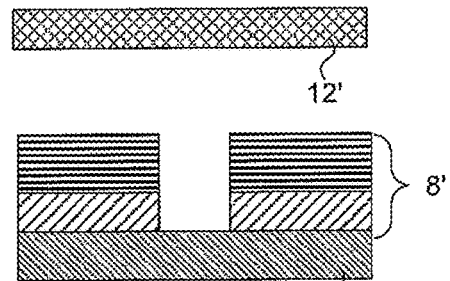
Figure 1F:
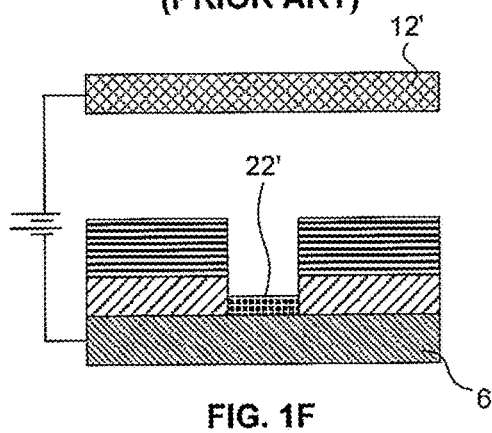
Figure 1G:
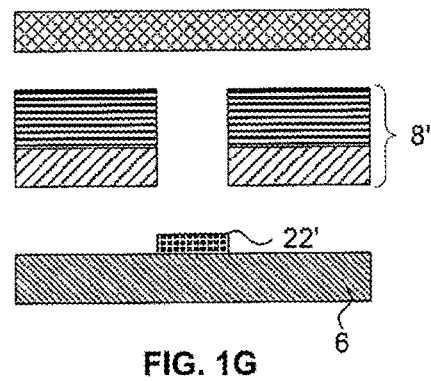
Figure 2A:
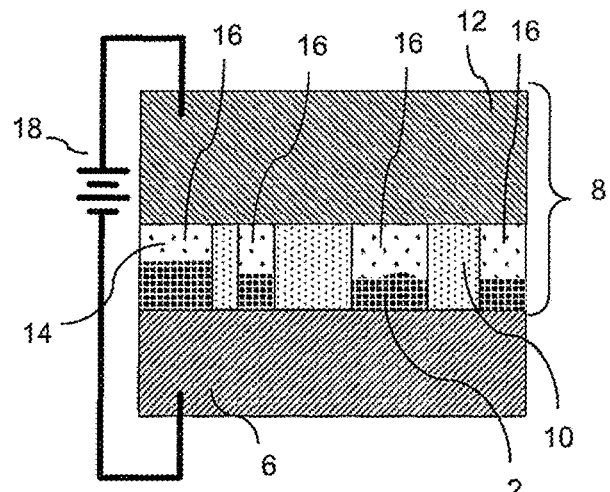
FIGS. 2A-2F schematically depict side views of various stages of an electrochemical fabrication process as applied to the formation of a particular structure where a sacrificial material is selectively deposited while a structural material is blanket deposited.
Figure 2B:
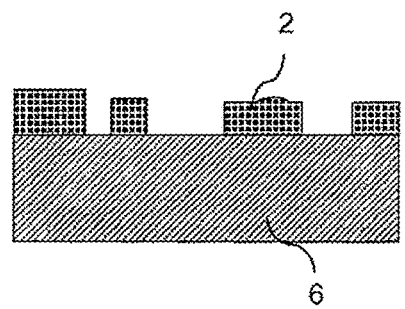
Figure 2C:
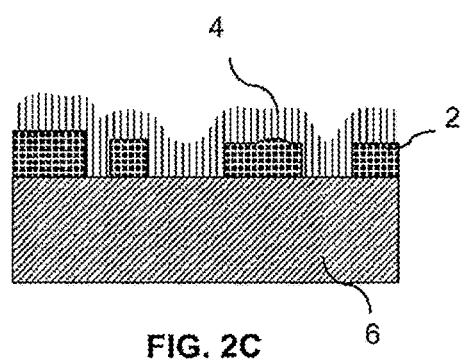
Figure 2D:
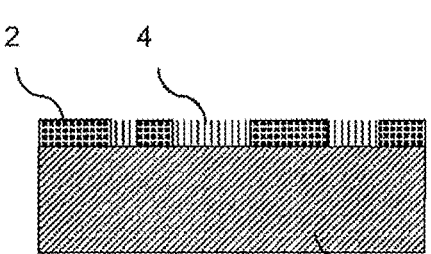
Figure 2E:
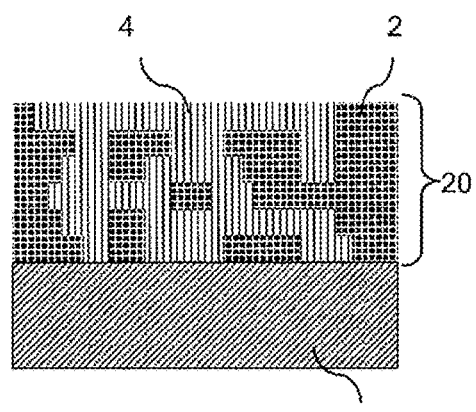
Figure 2F:
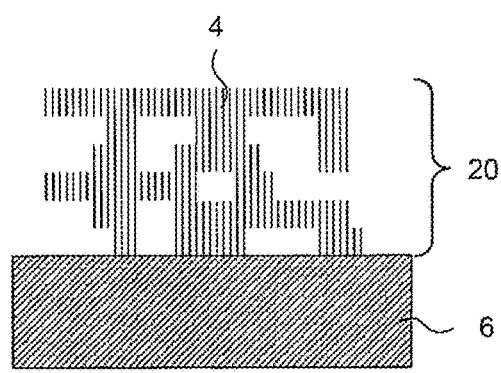
Figure 3A:
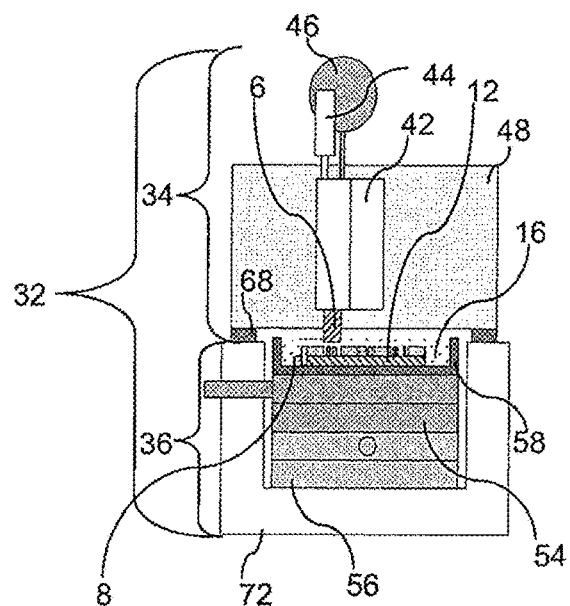
FIGS. 3A-3C schematically depict side views of various example subassemblies that may be used in manually implementing the electrochemical fabrication method depicted in FIGS. 2A-2F.
Figure 3B:
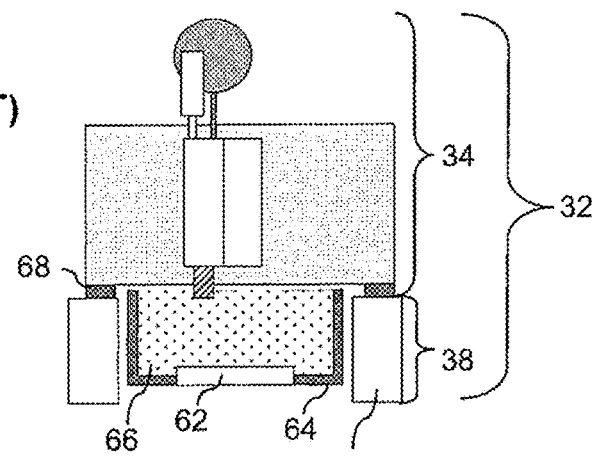
Figure 3C:
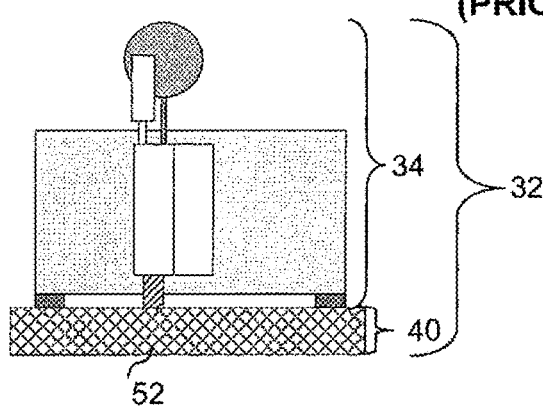
Figure 4A:
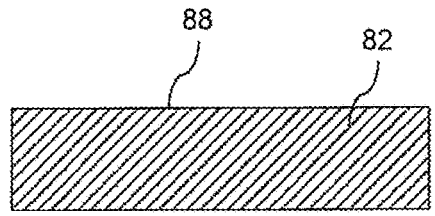
FIGS. 4A-4F schematically depict the formation of a first layer of a structure using adhered mask plating where the blanket deposition of a second material overlays both the openings between deposition locations of a first material and the first material itself
Figure 4B:
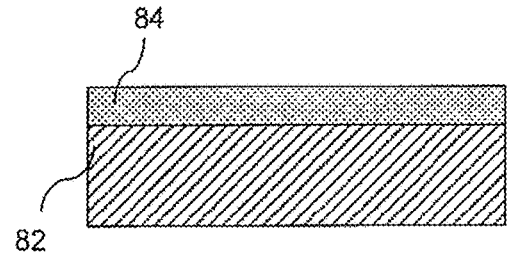
Figure 4C:
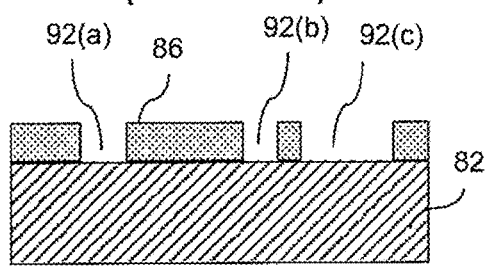
Figure 4D:
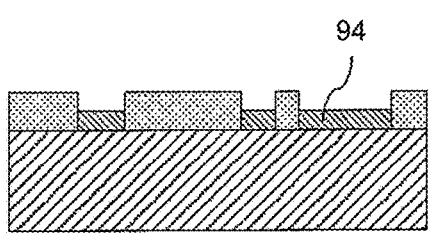
Figure 4E:
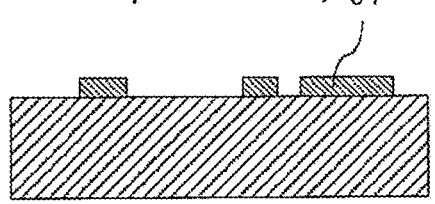
Figure 4F:
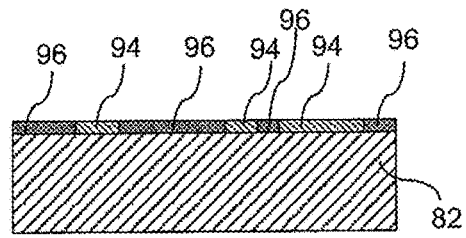
Figure 4G:
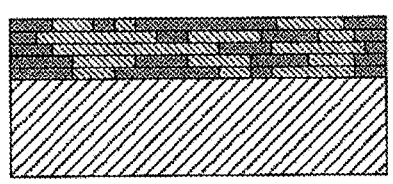
FIG. 4G depicts the completion of formation of the first layer resulting from planarizing the deposited materials to a desired level.
Figure 4H:
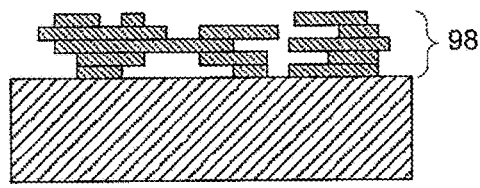
FIGS. 4H and 4I respectively depict the state of the process after formation of the multiple layers of the structure and after release of the structure from the sacrificial material.
Figure 4I:
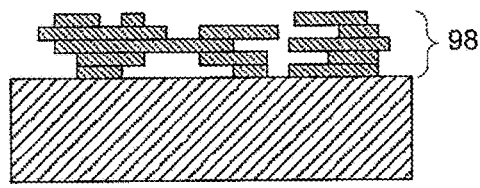

FIGS. 4A-4I illustrate various stages in the formation of a single layer of a multi-layer fabrication process where a second metal is deposited on a first metal as well as in openings in the first metal so that the first and second metal form part of the layer. In FIG. 4A a side view of a substrate 82 is shown, onto which patternable photoresist 84 is cast as shown in FIG. 4B. In FIG. 4C, a pattern of resist is shown that results from the curing, exposing, and developing of the resist. The patterning of the photoresist 84 results in openings or apertures 92(a)-92(c) extending from a surface 86 of the photoresist through the thickness of the photoresist to surface 88 of the substrate 82. In FIG. 4D a metal 94 (e.g. nickel) is shown as having been electroplated into the openings 92(a)-92(c). In FIG. 4E the photoresist has been removed (i.e. chemically stripped) from the substrate to expose regions of the substrate 82 which are not covered with the first metal 94. In FIG. 4F a second metal 96 (e.g. silver) is shown as having been blanket electroplated over the entire exposed portions of the substrate 82 (which is conductive) and over the first metal 94 (which is also conductive). FIG. 4G depicts the completed first layer of the structure which has resulted from the planarization of the first and second metals down to a height that exposes the first metal and sets a thickness for the first layer. In FIG. 4H the result of repeating the process steps shown in FIGS. 4B-4 G several times to form a multi-layer structure are shown where each layer consists of two materials. For most applications, one of these materials is removed as shown in FIG. 4I to yield a desired 3-D structure 98 (e.g. component or device).

Various embodiments of various aspects of the invention are directed to formation of three-dimensional structures from materials some of which may be electrodeposited or electroless deposited. Some of these structures may be formed form a single build level formed from one or more deposited materials while others are formed from a plurality of build layers each including at least two materials (e.g. two or more layers, more preferably five or more layers, and most preferably ten or more layers). In some embodiments, layer thicknesses may be as small as one micron or as large as fifty microns. In other embodiments, thinner layers may be used while in other embodiments, thicker layers may be used. In some embodiments structures having features positioned with micron level precision and minimum features size on the order of tens of microns are to be formed. In other embodiments structures with less precise feature placement and/or larger minimum features may be formed. In still other embodiments, higher precision and smaller minimum feature sizes may be desirable. In the present application meso-scale and millimeter scale have the same meaning and refer to devices that may have one or more dimensions extending into the 0.5-20 millimeter range, or somewhat larger and with features positioned with precision in the 10-100 micron range and with minimum features sizes on the order of 100 microns.

The various embodiments, alternatives, and techniques disclosed herein may form multi-layer structures using a single patterning technique on all layers or using different patterning techniques on different layers. For example, various embodiments of the invention may perform selective patterning operations using conformable contact masks and masking operations (i.e. operations that use masks which are contacted to but not adhered to a substrate), proximity masks and masking operations (i.e. operations that use masks that at least partially selectively shield a substrate by their proximity to the substrate even if contact is not made), non-conformable masks and masking operations (i.e. masks and operations based on masks whose contact surfaces are not significantly conformable), and/or adhered masks and masking operations (masks and operations that use masks that are adhered to a substrate onto which selective deposition or etching is to occur as opposed to only being contacted to it). Conformable contact masks, proximity masks, and non-conformable contact masks share the property that they are preformed and brought to, or in proximity to, a surface which is to be treated (i.e. the exposed portions of the surface are to be treated). These masks can generally be removed without damaging the mask or the surface that received treatment to which they were contacted, or located in proximity to. Adhered masks are generally formed on the surface to be treated (i.e. the portion of that surface that is to be masked) and bonded to that surface such that they cannot be separated from that surface without being completely destroyed damaged beyond any point of reuse. Adhered masks may be formed in a number of ways including (1) by application of a photoresist, selective exposure of the photoresist, and then development of the photoresist, (2) selective transfer of pre-patterned masking material, and/or (3) direct formation of masks from computer controlled depositions of material.

Patterning operations may be used in selectively depositing material and/or may be used in the selective etching of material. Selectively etched regions may be selectively filled in or filled in via blanket deposition, or the like, with a different desired material. In some embodiments, the layer-by-layer build up may involve the simultaneous formation of portions of multiple layers. In some embodiments, depositions made in association with some layer levels may result in depositions to regions associated with other layer levels (i.e. regions that lie within the top and bottom boundary levels that define a different layer's geometric configuration). Such use of selective etching and interlaced material deposition in association with multiple layers is described in U.S. patent application Ser. No. 10/434,519, by Smalley, now U.S. Pat. No. 7,252,861, and entitled "Methods of and Apparatus for Electrochemically Fabricating Structures Via Interlaced Layers or Via Selective Etching and Filling of Voids layer elements" which is hereby incorporated herein by reference as if set forth in full.

Temporary substrates on which structures may be formed may be of the sacrificial-type (i.e. destroyed or damaged during separation of deposited materials to the extent they can not be reused), non-sacrificial-type (i.e. not destroyed or excessively damaged, i.e. not damaged to the extent they may not be reused, e.g. with a sacrificial or release layer located between the substrate and the initial layers of a structure that is formed). Non-sacrificial substrates may be considered reusable, with little or no rework (e.g. replanarizing one or more selected surfaces or applying a release layer, and the like) though they may or may not be reused for a variety of reasons.

Definitions

This section of the specification is intended to set forth definitions for a number of specific terms that may be useful in describing the subject matter of the various embodiments of the invention. It is believed that the meanings of most if not all of these terms is clear from their general use in the specification but they are set forth hereinafter to remove any ambiguity that may exist. It is intended that these definitions be used in understanding the scope and limits of any claims that use these specific terms. As far as interpretation of the claims of this patent disclosure are concerned, it is intended that these definitions take presence over any contradictory definitions or allusions found in any materials which are incorporated herein by reference.

"Build" as used herein refers, as a verb, to the process of building a desired structure or plurality of structures from a plurality of applied or deposited materials which are stacked and adhered upon application or deposition or, as a noun, to the physical structure or structures formed from such a process. Depending on the context in which the term is used, such physical structures may include a desired structure embedded within a sacrificial material or may include only desired physical structures which may be separated from one another or may require dicing and/or slicing to cause separation.

"Build axis" or "build orientation" is the axis or orientation that is substantially perpendicular to substantially planar levels of deposited or applied materials that are used in building up a structure. The planar levels of deposited or applied materials may be or may not be completely planar but are substantially so in that the overall extent of their cross-sectional dimensions are significantly greater than the height of any individual deposit or application of material (e.g. 100, 500, 1000, 5000, or more times greater). The planar nature of the deposited or applied materials may come about from use of a process that leads to planar deposits or it may result from a planarization process (e.g. a process that includes mechanical abrasion, e.g. lapping, fly cutting, grinding, or the like) that is used to remove material regions of excess height. Unless explicitly noted otherwise, "vertical" as used herein refers to the build axis or nominal build axis (if the layers are not stacking with perfect registration) while "horizontal" refers to a direction within the plane of the layers (i.e. the plane that is substantially perpendicular to the build axis).

"Build layer" or "layer of structure" as used herein does not refer to a deposit of a specific material but instead refers to a region of a build located between a lower boundary level and an upper boundary level which generally defines a single cross-section of a structure being formed or structures which are being formed in parallel. Depending on the details of the actual process used to form the structure, build layers are generally formed on and adhered to previously formed build layers. In some processes the boundaries between build layers are defined by planarization operations which result in successive build layers being formed on substantially planar upper surfaces of previously formed build layers. In some embodiments, the substantially planar upper surface of the preceding build layer may be textured to improve adhesion between the layers. In other build processes, openings may exist in or be formed in the upper surface of a previous but only partially formed build layers such that the openings in the previous build layers are filled with materials deposited in association with current build layers which will cause interlacing of build layers and material deposits. Such interlacing is described in U.S. patent application Ser. No. 10/434,519 now U.S. Pat. No. 7,252,861. This referenced application is incorporated herein by reference as if set forth in full. In most embodiments, a build layer includes at least one primary structural material and at least one primary sacrificial material. However, in some embodiments, two or more primary structural materials may used without a primary sacrificial material (e.g. when one primary structural material is a dielectric and the other is a conductive material). In some embodiments, build layers are distinguishable from each other by the source of the data that is used to yield patterns of the deposits, applications, and/or etchings of material that form the respective build layers. For example, data descriptive of a structure to be formed which is derived from data extracted from different vertical levels of a data representation of the structure define different build layers of the structure. The vertical separation of successive pairs of such descriptive data may define the thickness of build layers associated with the data. As used herein, at times, "build layer" may be loosely referred simply as "layer". In many embodiments, deposition thickness of primary structural or sacrificial materials (i.e. the thickness of any particular material after it is deposited) is generally greater than the layer thickness and a net deposit thickness is set via one or more planarization processes which may include, for example, mechanical abrasion (e.g. lapping, fly cutting, polishing, and the like) and/or chemical etching (e.g. using selective or non-selective etchants). The lower boundary and upper boundary for a build layer may be set and defined in different ways. From a design point of view they may be set based on a desired vertical resolution of the structure (which may vary with height). From a data manipulation point of view, the vertical layer boundaries may be defined as the vertical levels at which data descriptive of the structure is processed or the layer thickness may be defined as the height separating successive levels of cross-sectional data that dictate how the structure will be formed. From a fabrication point of view, depending on the exact fabrication process used, the upper and lower layer boundaries may be defined in a variety of different ways. For example by planarization levels or effective planarization levels (e.g. lapping levels, fly cutting levels, chemical mechanical polishing levels, mechanical polishing levels, vertical positions of structural and/or sacrificial materials after relatively uniform etch back following a mechanical or chemical mechanical planarization process). For example, by levels at which process steps or operations are repeated. At levels at which, at least theoretically, lateral extends of structural material can be changed to define new cross-sectional features of a structure.

"Layer thickness" is the height along the build axis between a lower boundary of a build layer and an upper boundary of that build layer.

"Planarization" is a process that tends to remove materials, above a desired plane, in a substantially non-selective manner such that all deposited materials are brought to a substantially common height or desired level (e.g. within 20%, 10%, 5%, or even 1% of a desired layer boundary level). For example, lapping removes material in a substantially non-selective manner though some amount of recession one material or another may occur (e.g. copper may recess relative to nickel). Planarization may occur primarily via mechanical means, e.g. lapping, grinding, fly cutting, milling, sanding, abrasive polishing, frictionally induced melting, other machining operations, or the like (i.e. mechanical planarization). Mechanical planarization maybe followed or proceeded by thermally induced planarization (e.g. melting) or chemically induced planarization (e.g.

etching). Planarization may occur primarily via a chemical and/or electrical means (e.g. chemical etching, electrochemical etching, or the like). Planarization may occur via a simultaneous combination of mechanical and chemical etching (e.g. chemical mechanical polishing (CMP)).

"Structural material" as used herein refers to a material that remains part of the structure when put into use.

"Supplemental structural material" as used herein refers to a material that forms part of the structure when the structure is put to use but is not added as part of the build layers but instead is added to a plurality of layers simultaneously (e.g. via one or more coating operations that applies the material, selectively or in a blanket fashion, to a one or more surfaces of a desired build structure that has been released from a sacrificial material.

"Primary structural material" as used herein is a structural material that forms part of a given build layer and which is typically deposited or applied during the formation of that build layer and which makes up more than 20% of the structural material volume of the given build layer. In some embodiments, the primary structural material may be the same on each of a plurality of build layers or it may be different on different build layers. In some embodiments, a given primary structural material may be formed from two or more materials by the alloying or diffusion of two or more materials to form a single material.

"Secondary structural material" as used herein is a structural material that forms part of a given build layer and is typically deposited or applied during the formation of the given build layer but is not a primary structural material as it individually accounts for only a small volume of the structural material associated with the given layer. A secondary structural material will account for less than 20% of the volume of the structural material associated with the given layer. In some preferred embodiments, each secondary structural material may account for less than 10%, 5%, or even 2% of the volume of the structural material associated with the given layer. Examples of secondary structural materials may include seed layer materials, adhesion layer materials, barrier layer materials (e.g. diffusion barrier material), and the like. These secondary structural materials are typically applied to form coatings having thicknesses less than 2 microns, 1 micron, 0.5 microns, or even 0.2 microns). The coatings may be applied in a conformal or directional manner (e.g. via CVD, PVD, electroless deposition, or the like). Such coatings may be applied in a blanket manner or in a selective manner. Such coatings may be applied in a planar manner (e.g. over previously planarized layers of material) as taught in U.S. patent application Ser. No. 10/607,931, now U.S. Pat. No. 7,239,219. In other embodiments, such coatings may be applied in a non-planar manner, for example, in openings in and over a patterned masking material that has been applied to previously planarized layers of material as taught in U.S. patent application Ser. No. 10/841,383, now U.S. Pat. No. 7,195,989. These referenced applications are incorporated herein by reference as if set forth in full herein.

"Functional structural material" as used herein is a structural material that would have been removed as a sacrificial material but for its actual or effective encapsulation by other structural materials. Effective encapsulation refers, for example, to the inability of an etchant to attack the functional structural material due to inaccessibility that results from a very small area of exposure and/or due to an elongated or tortuous exposure path. For example, large (10,000 $\mu m^2$) but thin (e.g. less than 0.5 microns) regions of sacrificial copper sandwiched between deposits of nickel may define regions of functional structural material depending on ability of a release etchant to remove the sandwiched copper.

"Sacrificial material" is material that forms part of a build layer but is not a structural material. Sacrificial material on a given build layer is separated from structural material on that build layer after formation of that build layer is completed and more generally is removed from a plurality of layers after completion of the formation of the plurality of layers during a "release" process that removes the bulk of the sacrificial material or materials. In general sacrificial material is located on a build layer during the formation of one, two, or more subsequent build layers and is thereafter removed in a manner that does not lead to a planarized surface. Materials that are applied primarily for masking purposes, i.e. to allow subsequent selective deposition or etching of a material, e.g. photoresist that is used in forming a build layer but does not form part of the build layer) or that exist as part of a build for less than one or two complete build layer formation cycles are not considered sacrificial materials as the term is used herein but instead shall be referred as masking materials or as temporary materials. These separation processes are sometimes referred to as a release process and may or may not involve the separation of structural material from a build substrate. In many embodiments, sacrificial material within a given build layer is not removed until all build layers making up the three-dimensional structure have been formed. Of course sacrificial material may be, and typically is, removed from above the upper level of a current build layer during planarization operations during the formation of the current build layer. Sacrificial material is typically removed via a chemical etching operation but in some embodiments may be removed via a melting operation or electrochemical etching operation. In typical structures, the removal of the sacrificial material (i.e. release of the structural material from the sacrificial material) does not result in planarized surfaces but instead results in surfaces that are dictated by the boundaries of structural materials located on each build layer. Sacrificial materials are typically distinct from structural materials by having different properties therefrom (e.g. chemical etchability, hardness, melting point, etc.) but in some cases, as noted previously, what would have been a sacrificial material may become a structural material by its actual or effective encapsulation by other structural materials. Similarly, structural materials may be used to form sacrificial structures that are separated from a desired structure during a release process via the sacrificial structures being only attached to sacrificial material or potentially by dissolution of the sacrificial structures themselves using a process that is insufficient to reach structural material that is intended to form part of a desired structure. It should be understood that in some embodiments, small amounts of structural material may be removed, after or during release of sacrificial material. Such small amounts of structural material may have been inadvertently formed due to imperfections in the fabrication process or may result from the proper application of the process but may result in features that are less than optimal (e.g. layers with stairs steps in regions where smooth sloped surfaces are desired. In such cases the volume of structural material removed is typically minuscule compared to the amount that is retained and thus such removal is ignored when labeling materials as sacrificial or structural. Sacrificial materials are typically removed by a dissolution process, or the like, that destroys the geometric configuration of the sacrificial material as it existed on the build layers. In many embodiments, the sacrificial material is a conductive material such as a metal. As will be discussed hereafter, masking materials though typically sacrificial in nature are not termed sacrificial materials herein unless they meet the required definition of sacrificial material.

"Supplemental sacrificial material" as used herein refers to a material that does not form part of the structure when the structure is put to use and is not added as part of the build layers but instead is added to a plurality of layers simultaneously (e.g. via one or more coating operations that applies the material, selectively or in a blanket fashion, to a one or more surfaces of a desired build structure that has been released from an initial sacrificial material. This supplemental sacrificial material will remain in place for a period of time and/or during the performance of certain post layer formation operations, e.g. to protect the structure that was released from a primary sacrificial material, but will be removed prior to putting the structure to use.

"Primary sacrificial material" as used herein is a sacrificial material that is located on a given build layer and which is typically deposited or applied during the formation of that build layer and which makes up more than 20% of the sacrificial material volume of the given build layer. In some embodiments, the primary sacrificial material may be the same on each of a plurality of build layers or may be different on different build layers. In some embodiments, a given primary sacrificial material may be formed from two or more materials by the alloying or diffusion of two or more materials to form a single material.

"Secondary sacrificial material" as used herein is a sacrificial material that is located on a given build layer and is typically deposited or applied during the formation of the build layer but is not a primary sacrificial materials as it individually accounts for only a small volume of the sacrificial material associated with the given layer. A secondary sacrificial material will account for less than 20% of the volume of the sacrificial material associated with the given layer. In some preferred embodiments, each secondary sacrificial material may account for less than 10%, 5%, or even 2% of the volume of the sacrificial material associated with the given layer. Examples of secondary structural materials may include seed layer materials, adhesion layer materials, barrier layer materials (e.g. diffusion barrier material), and the like. These secondary sacrificial materials are typically applied to form coatings having thicknesses less than 2 microns, 1 micron, 0.5 microns, or even 0.2 microns). The coatings may be applied in a conformal or directional manner (e.g. via CVD, PVD, electroless deposition, or the like). Such coatings may be applied in a blanket manner or in a selective manner. Such coatings may be applied in a planar manner (e.g. over previously planarized layers of material) as taught in U.S. patent application Ser. No. 10/607,931, now U.S. Pat. No. 7,239,219. In other embodiments, such coatings may be applied in a non-planar manner, for example, in openings in and over a patterned masking material that has been applied to previously planarized layers of material as taught in U.S. patent application Ser. No. 10/841,383, now U.S. Pat. No. 7,195,989. These referenced applications are incorporated herein by reference as if set forth in full herein.

"Adhesion layer", "seed layer", "barrier layer", and the like refer to coatings of material that are thin in comparison to the layer thickness and thus generally form secondary structural material portions or sacrificial material portions of some layers. Such coatings may be applied uniformly over a previously formed build layer, they may be applied over a portion of a previously formed build layer and over patterned structural or sacrificial material existing on a current (i.e. partially formed) build layer so that a non-planar seed layer results, or they may be selectively applied to only certain locations on a previously formed build layer. In the event such coatings are non-selectively applied, selected portions may be removed (1) prior to depositing either a sacrificial material or structural material as part of a current layer or (2) prior to beginning formation of the next layer or they may remain in place through the layer build up process and then etched away after formation of a plurality of build layers.

"Masking material" is a material that may be used as a tool in the process of forming a build layer but does not form part of that build layer. Masking material is typically a photopolymer or photoresist material or other material that may be readily patterned. Masking material is typically a dielectric. Masking material, though typically sacrificial in nature, is not a sacrificial material as the term is used herein. Masking material is typically applied to a surface during the formation of a build layer for the purpose of allowing selective deposition, etching, or other treatment and is removed either during the process of forming that build layer or immediately after the formation of that build layer.

"Multilayer structures" are structures formed from multiple build layers of deposited or applied materials.

"Multilayer three-dimensional (or 3D or 3-D) structures" are Multilayer Structures that meet at least one of two criteria: (1) the structural material portion of at least two layers of which one has structural material portions that do not overlap structural material portions of the other.

"Complex multilayer three-dimensional (or 3D or 3-D) structures" are multilayer three-dimensional structures formed from at least three layers where a line may be defined that hypothetically extends vertically through at least some portion of the build layers of the structure will extend from structural material through sacrificial material and back through structural material or will extend from sacrificial material through structural material and back through sacrificial material (these might be termed vertically complex multilayer three-dimensional structures). Alternatively, complex multilayer three-dimensional structures may be defined as multilayer three-dimensional structures formed from at least two layers where a line may be defined that hypothetically extends horizontally through at least some portion of a build layer of the structure that will extend from structural material through sacrificial material and back through structural material or will extend from sacrificial material through structural material and back through sacrificial material (these might be termed horizontally complex multilayer three-dimensional structures). Worded another way, in complex multilayer three-dimensional structures, a vertically or horizontally extending hypothetical line will extend from one or structural material or void (when the sacrificial material is removed) to the other of void or structural material and then back to structural material or void as the line is traversed along at least a portion of the line.

"Moderately complex multilayer three-dimensional (or 3D or 3-D) structures are complex multilayer 3D structures for which the alternating of void and structure or structure and void not only exists along one of a vertically or horizontally extending line but along lines extending both vertically and horizontally.

"Highly complex multilayer (or 3D or 3-D) structures are complex multilayer 3D structures for which the structure-to-void-to-structure or void-to-structure-to-void alternating occurs once along the line but occurs a plurality of times along a definable horizontally or vertically extending line.

"Up-facing feature" is an element dictated by the cross-sectional data for a given build layer "n" and a next build layer "n+1" that is to be formed from a given material that exists on the build layer "n" but does not exist on the immediately succeeding build layer "n+1". For convenience the term "up-facing feature" will apply to such features regardless of the build orientation.

"Down-facing feature" is an element dictated by the cross-sectional data for a given build layer "n" and a preceding build layer "n−1" that is to be formed from a given material that exists on build layer "n" but does not exist on the immediately preceding build layer "n−1". As with up-facing features, the term "down-facing feature" shall apply to such features regardless of the actual build orientation.

"Continuing region" is the portion of a given build layer "n" that is dictated by the cross-sectional data for the given build layer "n", a next build layer "n+1" and a preceding build layer "n−1" that is neither up-facing nor down-facing for the build layer "Minimum feature size" or "MFS" refers to a necessary or desirable spacing between structural material elements on a given layer that are to remain distinct in the final device configuration. If the minimum feature size is not maintained for structural material elements on a given layer, the fabrication process may result in structural material inadvertently bridging what were intended to be two distinct elements (e.g. due to masking material failure or failure to appropriately fill voids with sacrificial material during formation of the given layer such that during formation of a subsequent layer structural material inadvertently fills the void). More care during fabrication can lead to a reduction in minimum feature size. Alternatively, a willingness to accept greater losses in productivity (i.e. lower yields) can result in a decrease in the minimum feature size. However, during fabrication for a given set of process parameters, inspection diligence, and yield (successful level of production) a minimum design feature size is set in one way or another. The above described minimum feature size may more appropriately be termed minimum feature size of gaps or voids (e.g. the MFS for sacrificial material regions when sacrificial material is deposited first). Conversely a minimum feature size for structure material regions (minimum width or length of structural material elements) may be specified. Depending on the fabrication method and order of deposition of structural material and sacrificial material, the two types of minimum feature sizes may be the same or different. In practice, for example, using electrochemical fabrication methods as described herein, the minimum features size on a given layer may be roughly set to a value that approximates the layer thickness used to form the layer and it may be considered the same for both structural and sacrificial material widths. In some more rigorously implemented processes (e.g. with higher examination regiments and tolerance for rework), it may be set to an amount that is 80%, 50%, or even 30% of the layer thickness. Other values or methods of setting minimum feature sizes may be used. Worded another way, depending on the geometry of a structure, or plurality of structures, being formed, the structure, or structures, may include elements (e.g. solid regions) which have dimensions smaller than a first minimum feature size and/or have spacings, voids, openings, or gaps (e.g. hollow or empty regions) located between elements, where the spacings are smaller than a second minimum feature size where the first and second minimum feature sizes may be the same or different and where the minimum feature sizes represent lower limits at which formation of elements and/or spacing can be reliably formed. Reliable formation refers to the ability to accurately form or produce a given geometry of an element, or of the spacing between elements, using a given formation process, with a minimum acceptable yield. The minimum acceptable yield may depend on a number of factors including: (1) number of features present per layer, (2) numbers of layers, (3) the criticality of the successful formation of each feature, (4) the number and severity of other factors effecting overall yield, and (5) the desired or required overall yield for the structures or devices themselves. In some circumstances, the minimum size may be determined by a yield requirement per feature which is as low as 70%, 60%, or even 50%. While in other circumstances the yield requirement per feature may be as high as 90%, 95%, 99%, or even higher. In some circumstances (e.g. in producing a filter element) the failure to produce a certain number of desired features (e.g. 20-40% failure may be acceptable while in an electrostatic actuator the failure to produce a single small space between two moveable electrodes may result in failure of the entire device. The MFS, for example, may be defined as the minimum width of a narrow and processing element (e.g. photoresist element or sacrificial material element) or structural element (e.g. structural material element) that may be reliably formed (e.g. 90-99.9 times out of 100) which is either independent of any wider structures or has a substantial independent length (e.g. 200-1000 microns) before connecting to a wider region.

"Sublayer" as used herein refers to a portion of a build layer that typically includes the full lateral extents of that build layer but only a portion of its height. A sublayer is usually a vertical portion of build layer that undergoes independent processing compared to another sublayer of that build layer.

Tissue Approximation Devices, Methods for Use, and Methods for Making

Previous designs of tissue approximation devices are set forth in U.S. patent application Ser. Nos. 11/591,911, 11/598,968, 11/625,807, and 12/346,034. Each of these referenced applications is hereby incorporated herein by reference as if set forth in full.

Figure 5:
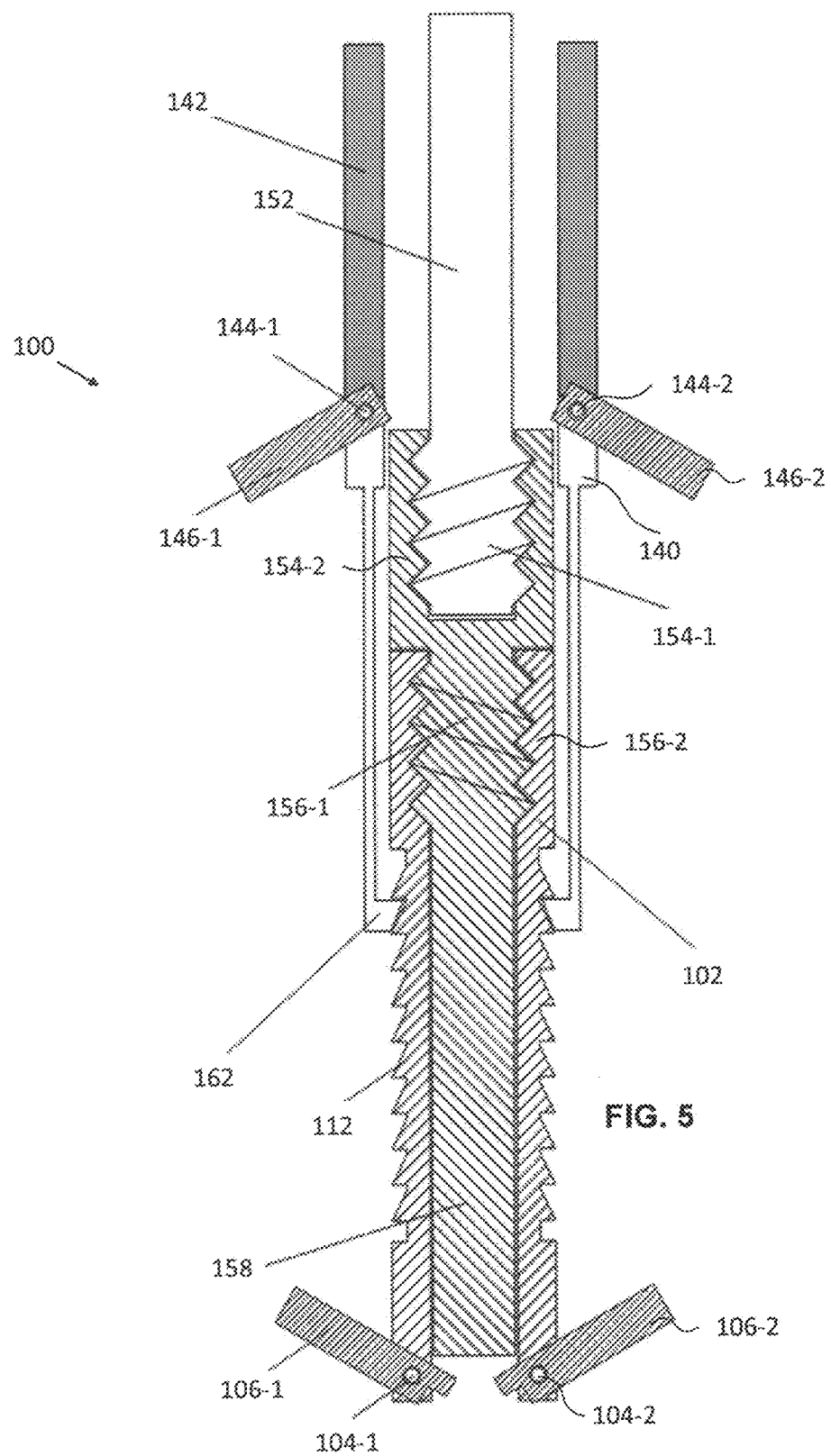
FIG. 5 depicts the device 100 of the first embodiment along with a push tube 142 and a control wire 152 that has right hand threads 154 on its distal end.

Herein after, two primary device embodiments and one method of use embodiment are described. FIG. 5 depicts the device 100 of the first embodiment along with a push tube 142 and a control wire 152 that has right hand threads 154-1 on its distal end. The device 100 of this embodiment includes a number of elements: (1) distal expandable wings 106-1 and 106-2; (2) proximal expanding wings 146-1 and 146-2, (3) a distal body portion 102 in the form of a rail including teeth 112 for engaging a ratcheting catch 162, a proximal end including a left handed threaded female receptacle 156-2 for engaging left handed male threaded element 156-1 located between a translatable stop bar 158 and right hand threaded female control wire receptacle 154-2, a distal end to which distal wings 106-1 and 106-2 are pivotably mounted via pivots 104-1 and 104-2, (4) a more proximal body portion 140 in the form of proximal sleeve to which wings 146-1 and 146-2 mount via pivots 144-1 and 144-2 and from which deflection arms distally extend to catch heads 162 wherein the proximal body portion can ratchetably slide longitudinally relative to the more distal body portion 102 to bring the distal and proximal wings into closer proximity. The device also includes a stop bar 158 having an intermediate left hand threaded element or portion 156-1 that rotatably engages a left-handed threaded element 156-2 of the proximal body portion with the threaded element giving way more proximally to a right handed female threaded receptacle 154-2 that engaged the right handed threaded element 154-1 of the control wire 152. While located in one position (i.e. a more distal position relative to body portion 102) the stop inhibits the distal wings from opening beyond a perpendicular orientation but while in a second position (i.e. a retracted or more proximal position) the stop allows the distal wings 106-1 and 106-2 to rotate past the perpendicular to collapse distally to a more axial orientation beyond the distal wing pivots 104-1 and 104-2. Upon rotating the wire counterclockwise relative to the stop, the wire can be disengaged from its retained position. On the other hand, rotating the wire clockwise relative to the stop results in complete seating of the wire and eventual rotation of the stop relative to the distal body which, because of the left handed threading, can result in the proximal movement of the stop and the distal collapse of the distal wing elements.

Figure 6A:
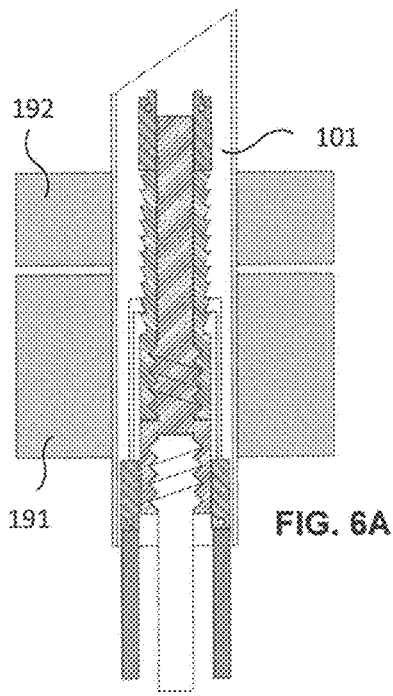
FIGS. 6A-6D depict the states of a process for using the device of FIG. 5 in approximating two tissue elements which can be followed by removal of the wire and removal of the push tube.
Figure 6B:
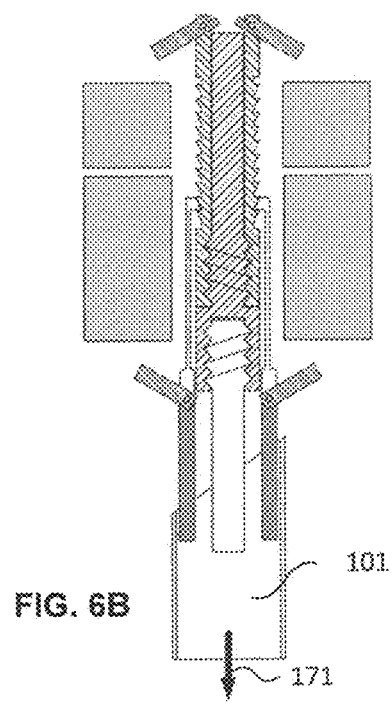
Figure 6C:
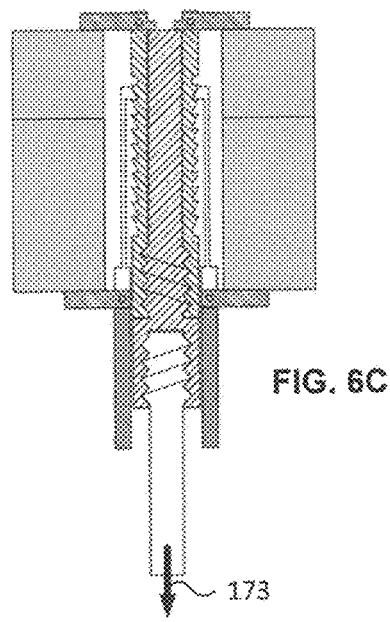
Figure 6D:
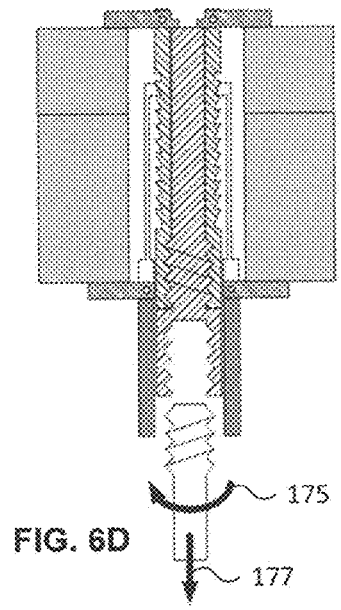

FIGS. 6A-6D depict the states of a process for using the device of FIG. 5 in approximating two tissue elements which can be followed by removal of the wire and removal of the push tube. FIG. 6A depicts the state of the process after insertion of a needle 101 carrying the approximation device 100 through both the proximal tissue 191 and the distal tissue 192. FIG. 6B depicts the state of the process after withdrawal of the needle 101 in direction 171 allowing the distal and proximal wings of device 100 to open on opposite sides of the tissue elements. FIG. 6C depicts the state of the process after the wire has been pulled in direction 173 relative to the push tube to cause approximation of the two tissue elements via the bringing together of the proximal and distal wings into more proximate positions. This more proximate positioning is held by the ratcheting rail of body portion 102 and catch mechanism associated with body portion 140. FIG. 6D depicts the state of the process after the wire has been rotated in counterclockwise direction 175 and moved in direction 177 to release it from the proximal end of the more proximal body. The tube may be retained by the device 100 in a variety of non-rotatable releasable ways, such as for example by both the tube and the proximal end of the proximal body portion containing flats or ridges that inhibit rotational motion by allow axial sliding during release. Sliding to release may be inhibited in a variety of ways, such as for example, by frictional force, break away tabs, flexures with retention notches that are inhibited from opening so long at the control wire is engaged.

FIGS. 7A-7B illustrate a process for releasing the device of FIG. 5 from tissue. FIG. 7A depicts the state of the process either before release of the wire or after reintroduction of the wire into the proximal end of the stop body via a clockwise rotation in direction 181 and after continued rotation in direction 181 to cause relative proximal motion in direction 183 of the stop relative to the body portions 102 and 163 and clearance between the stop and the inner ends of the distal wings. FIG. 7B depicts the state of the process after continued clockwise rotation of the wire relative to the approximation device such that the stop element is moved sufficiently proximally relative to the distal wings to allows for the collapse of the distal wings and the extraction of the approximation device by pulling in direction 185.

Figure 8A:
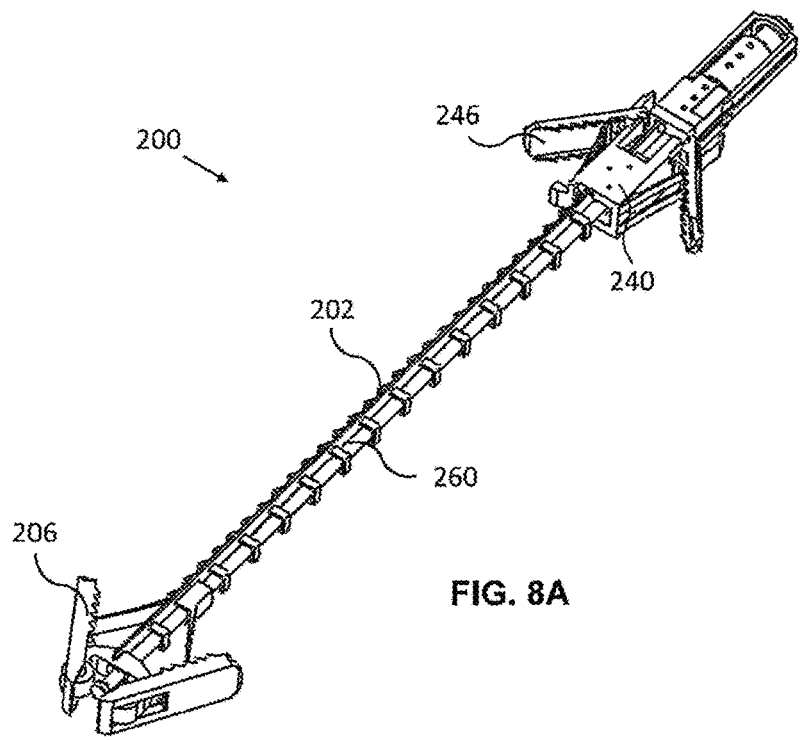
FIGS. 8A-8H provide various perspective views of the tissue approximation device of the second embodiment of the invention wherein the device is shown in various complete, close-up, and sectioned views as well as sectioned views.
Figure 8B:
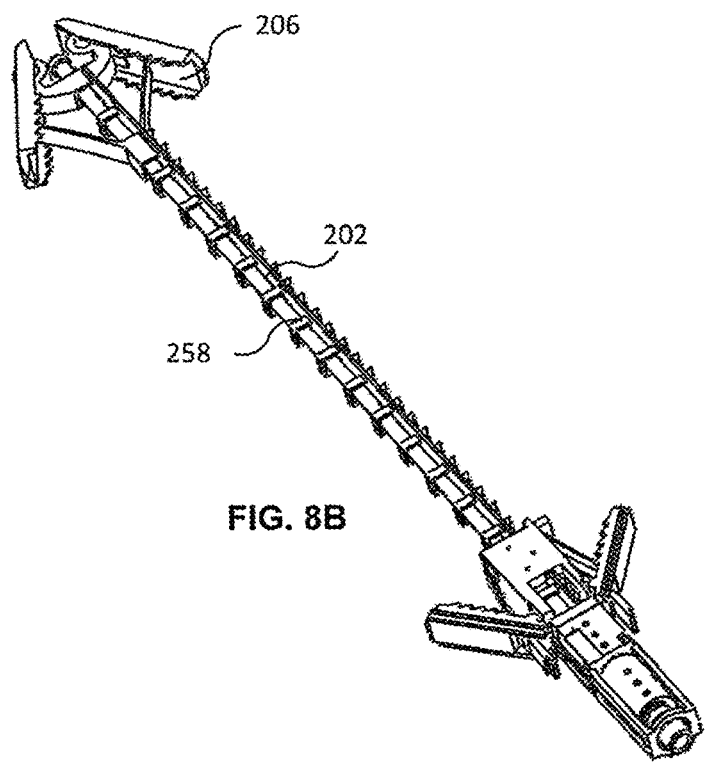
Figure 8C:
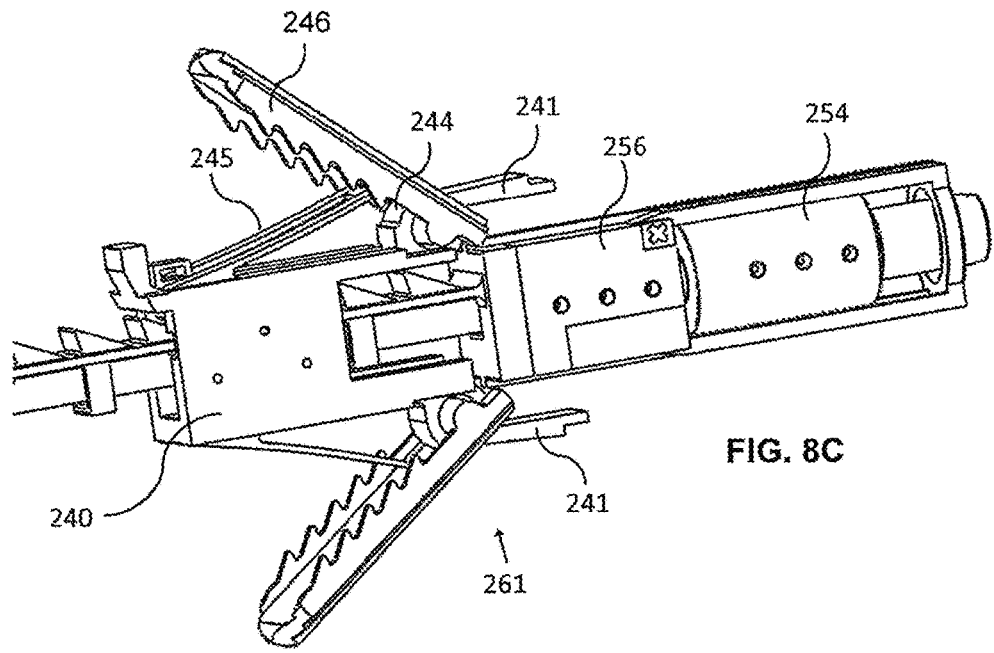
Figure 8D:
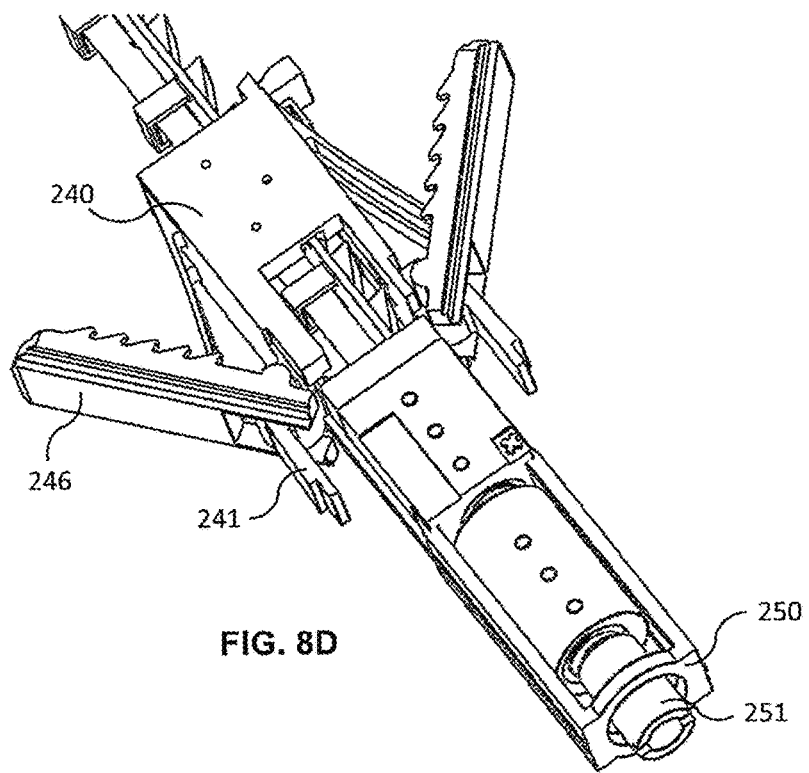
Figure 8E:
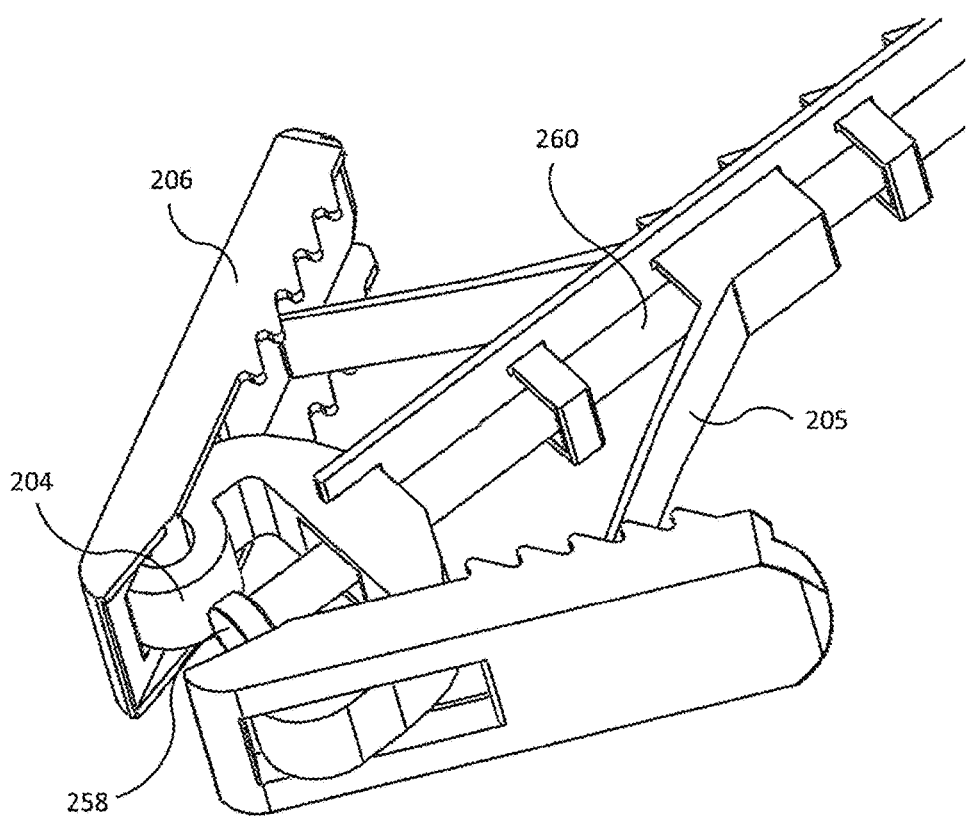
Figure 8F:
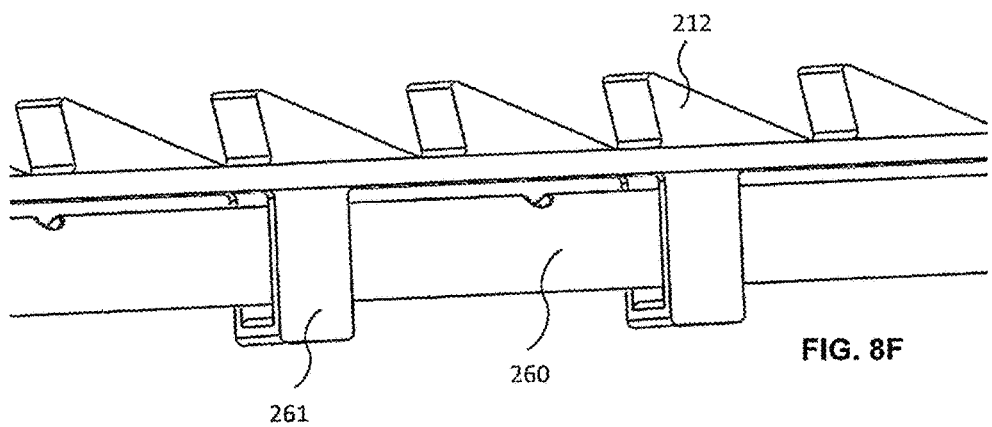
Figure 8G:
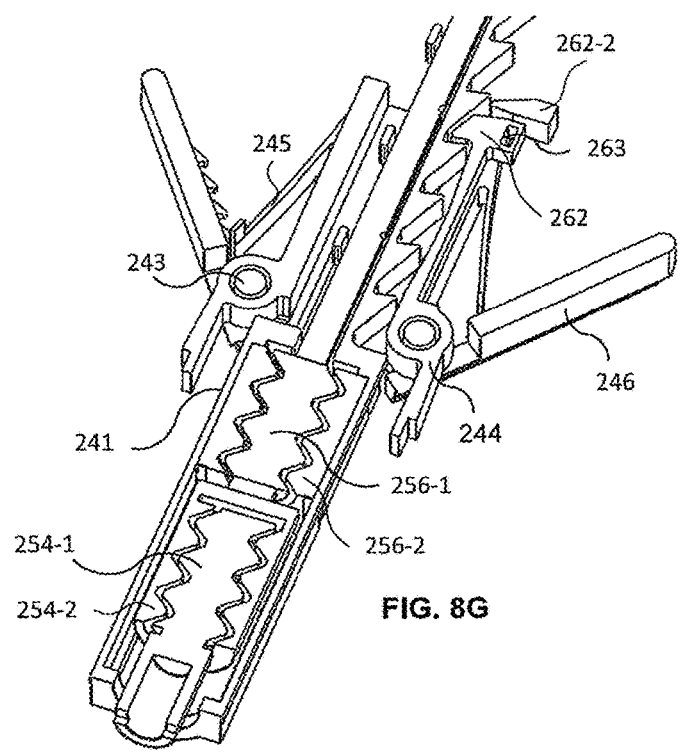
Figure 8H:
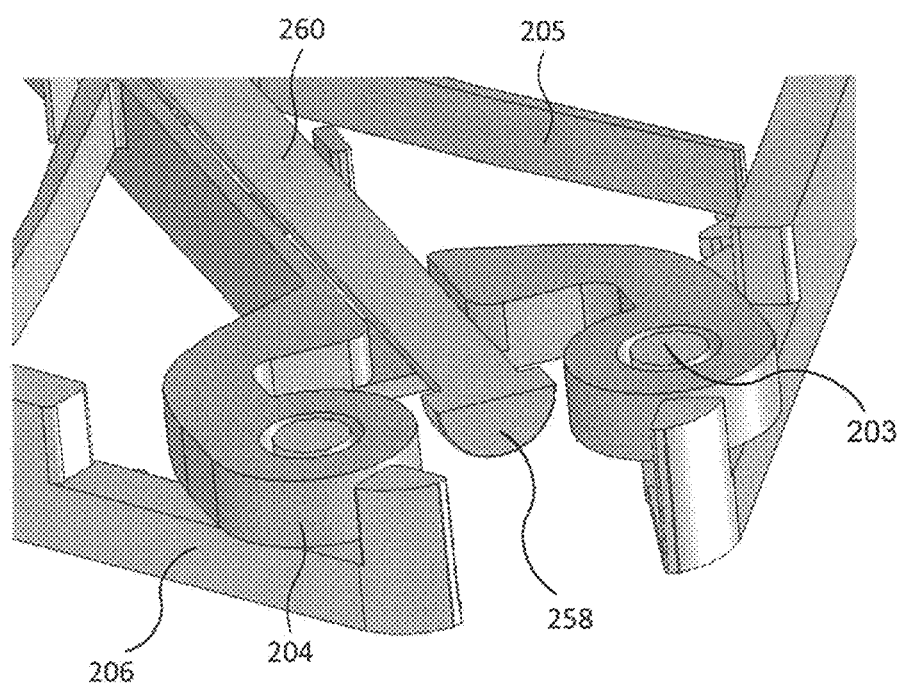
Figure 9:
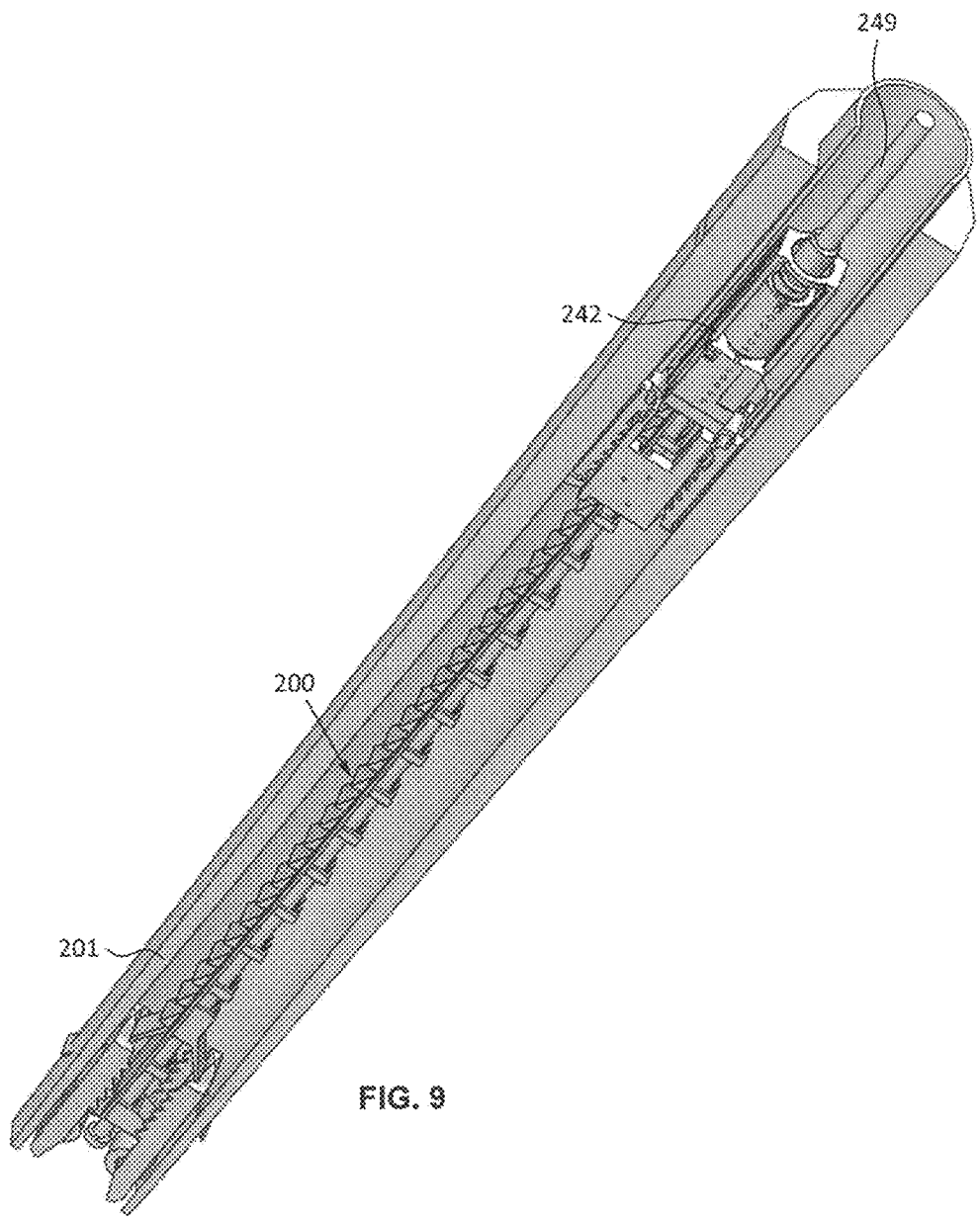
FIG. 9 provides a perspective section view of the tissue approximation device 200 located within a needle 201 and engaged with its push tube 242 and control wire 249.

FIGS. 8A-8H provide various perspective views of the tissue approximation device of the second embodiment of the invention wherein the device is shown in various complete, close-up, and sectioned views as well as sectioned views while FIG. 9 shows the device of FIGS. 8A-8H in conjunction with other elements with which it is combined to perform an approximation procedure.

FIGS. 8A and 8B show two different perspective views of an approximation device 200 according to a second device embodiment where distal wings 206 and proximal wings 246 can be seen along with central ratcheting rail 202, stop rod 260, and proximal body portion 240. FIGS. 8C-8H provide perspective and sectioned close up views of various components and features of the device 200. The proximal body portion 240 that holds the proximal wings 246 can move longitudinally or axially along the ratcheting rail 202 to positions more proximate to the distal wings 206. The rod element 260 at its distal end provides a stop 258 for preventing distal wings from opening too wide and on its proximal end forms a threaded female attachment area 254-2, for the right handed thread control wire coupler which includes threaded element 254-1 and sleeve 251, as well as providing a left-handed male thread element 256-1 that engages the proximal body, via left handed female thread region 256-2, that holds the proximal wings 246. As can be seen in FIGS. 8A and 8B the moveable rod is held to the ratcheting rail by a plurality of ring-like elements which ensure that the rod maintains the right positioning with regard to the rail so that the stop function for limiting the motion of distal wings can effectively occur.

FIGS. 8C and 8D provide different perspective close-up views of the proximal end of the device 200 where the slidable proximal body element 240 holding the proximal wings 246 can be seen along with a pusher tube interface 241 and left-handed and right-handed thread engagement areas 256 and 254. Springs 245 can be used to at least partially spread wings 246 by causing them to pivot about pivot rings 244.

FIG. 8E provides a close-up view of the distal end of the device 200 where the wing stop 258 may be seen along with deployment springs 205 that force the wings 206 to pivot about pivot rings 204 from a closed configuration (e.g. proximal axial alignment) to an at least partially open or radial configuration.

FIG. 8F provides a close-up view of the stop rod 260 and rod guide elements 261 that maintain the rod and ratcheting mechanisms in axially translatable positions while inhibiting other degrees of freedom.

FIG. 8G provides a sectioned perspective view of the proximal body portion and related element providing views of the right handed female threads 254-2 of the rod, the right handed male threads of the wire coupler 254-1, the left-handed male threads 256-1 of the rod, and left handed female threads 256-2 of the ratcheting rail, and catch head 262 with release feature 263 located at the distal end of a compliant arm (not labeled), secondary catch head 262-2, and spring 245 for at least partially spreading proximal wing 246 via rotation of pins 243 within proximal rings 244.

FIG. 8H provides a close-up sectioned perspective view of the distal end of the device whereby wings 206, wing pivot elements, including pivot ring 204, pivot pins 203, and expansion springs 205 can be seen along with the wing stop 258 and rod 260.

FIG. 9 provides a perspective section view of the tissue approximation device 200 located within a needle 201 and engaged with its push tube 242 and control wire 249. As can be seen the wings of the approximation device are pressed to axial positions by the inner wall of the needle.

Figure 10:
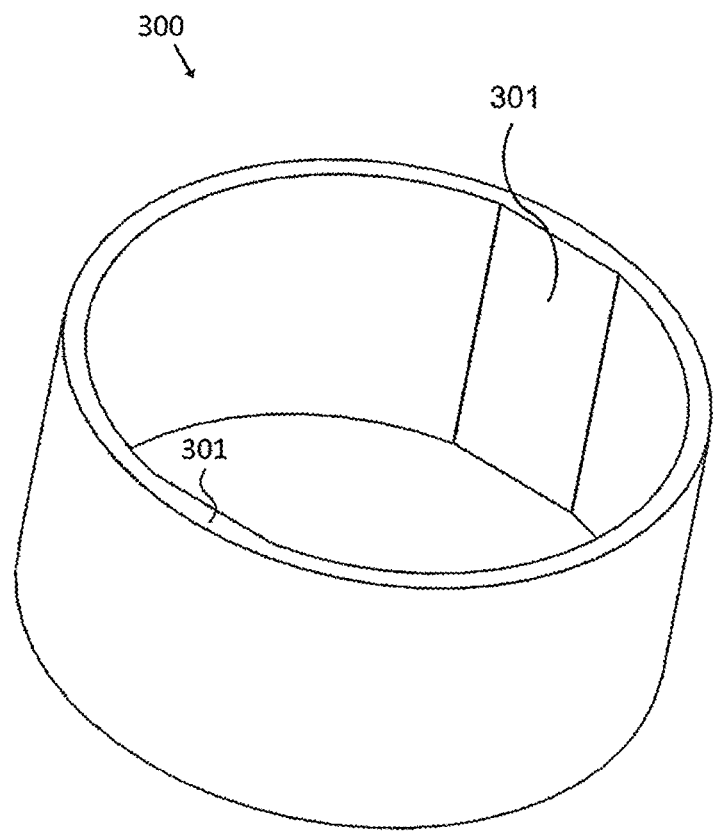
FIG. 10 provides a perspective view of an independently formed ring 300 for engaging a push tube and push tube interface arms.

FIG. 10 provides a perspective view of an independently formed ring 300 for engaging a push tube and push tube interface arms. The ring includes flats 301 for engaging flat surfaces of the push tube interface arms. This ring may be used as a coupling device for engaging a push tube 242 with the push tube interface 241 of FIGS. 8C and 8D. This device may be formed by electrochemical fabrication methods but for efficiency of formation is preferably formed separately from the instrument so that it may be formed with an optimal orientation, layer count, and the like. This coupling device may be bonded to the push tube and slid from the push tube interface arms when the procedure is completed. In some alternative embodiments, the pusher tube interface and/or the coupling device may be formed with slots and fingers for providing more rotational control than that which may be offered by the flats of the illustrated design. In still other embodiment the coupling mechanism may be bonded to the pusher tube interface in which case it would be releasably attached to the tube.

Numerous variation of the above described embodiment are possible and will be apparent to those of skill in the art upon review of the teachings herein. Some such variations are extractable for the teachings set forth in the various applications, patents, and papers incorporated herein by reference.

FURTHER COMMENTS AND CONCLUSIONS

Structural or sacrificial dielectric materials may be incorporated into embodiments of the present invention in a variety of different ways. Such materials may form a third material or higher deposited on selected layers or may form one of the first two materials deposited on some layers. Additional teachings concerning the formation of structures on dielectric substrates and/or the formation of structures that incorporate dielectric materials into the formation process and possibility into the final structures as formed are set forth in a number of patent applications filed Dec. 31, 2003. The first of these filings is U.S. Patent Application No. 60/534,184 which is entitled "Electrochemical Fabrication Methods Incorporating Dielectric Materials and/or Using Dielectric Substrates". The second of these filings is U.S. Patent Application No. 60/533,932, which is entitled "Electrochemical Fabrication Methods Using Dielectric Substrates". The third of these filings is U.S. Patent Application No. 60/534,157, which is entitled "Electrochemical Fabrication Methods Incorporating Dielectric Materials". The fourth of these filings is U.S. Patent Application No. 60/533,891, which is entitled "Methods for Electrochemically Fabricating Structures Incorporating Dielectric Sheets and/or Seed layers That Are Partially Removed Via Planarization". A fifth such filing is U.S. Patent Application No. 60/533,895, which is entitled "Electrochemical Fabrication Method for Producing Multi-layer Three-Dimensional Structures on a Porous Dielectric". Additional patent filings that provide teachings concerning incorporation of dielectrics into the EFAB process include U.S. patent application Ser. No. 11/139,262, filed May 26, 2005 by Lockard, et al., and which is entitled "Methods for Electrochemically Fabricating Structures Using Adhered Masks, Incorporating Dielectric Sheets, and/or Seed Layers that are Partially Removed Via Planarization"; and U.S. patent application Ser. No. 11/029,216, filed Jan. 3, 2005 by Cohen, et al., now abandoned, and which is entitled "Electrochemical Fabrication Methods Incorporating Dielectric Materials and/or Using Dielectric Substrates". These patent filings are each hereby incorporated herein by reference as if set forth in full herein.

Some embodiments may employ diffusion bonding or the like to enhance adhesion between successive layers of material. Various teachings concerning the use of diffusion bonding in electrochemical fabrication processes are set forth in U.S. patent application Ser. No. 10/841,384 which was filed May 7, 2004 by Cohen et al., now abandoned, which is entitled "Method of Electrochemically Fabricating Multilayer Structures Having Improved Interlayer Adhesion" and which is hereby incorporated herein by reference as if set forth in full. This application is hereby incorporated herein by reference as if set forth in full.

Some embodiments may incorporate elements taught in conjunction with other medical devices as set forth in various U.S. patent applications filed by the owner of the present application and/or may benefit from combined use with these other medical devices: Some of these alternative devices have been described in the following previously filed patent applications: (1) U.S. patent application Ser. No. 11/478,934, by Cohen et al., and entitled "Electrochemical Fabrication Processes Incorporating Non-Platable Materials and/or Metals that are Difficult to Plate On"; (2) U.S. patent application Ser. No. 11/582,049, by Cohen, and entitled "Discrete or Continuous Tissue Capture Device and Method for Making"; (3) U.S. patent application Ser. No. 11/625,807, by Cohen, and entitled "Microdevices for Tissue Approximation and Retention, Methods for Using, and Methods for Making"; (4) U.S. patent application Ser. No. 11/696,722, by Cohen, and entitled "Biopsy Devices, Methods for Using, and Methods for Making"; (5) U.S. patent application Ser. No. 11/734,273, by Cohen, and entitled "Thrombectomy Devices and Methods for Making"; (6) U.S. Patent Application No. 60/942,200, by Cohen, and entitled "Micro-Umbrella Devices for Use in Medical Applications and Methods for Making Such Devices"; and (7) U.S. patent application Ser. No. 11/444,999, by Cohen, and entitled "Microtools and Methods for Fabricating Such Tools". Each of these applications is incorporated herein by reference as if set forth in full herein.

Though the embodiments explicitly set forth herein have considered multi-material layers to be formed one after another. In some embodiments, it is possible to form structures on a layer-by-layer basis but to deviate from a strict planar layer on planar layer build up process in favor of a process that interlaces material between the layers. Such alternative build processes are disclosed in U.S. application Ser. No. 10/434,519, filed on May 7, 2003, now U.S. Pat. No. 7,252,861, entitled Methods of and Apparatus for Electrochemically Fabricating Structures Via Interlaced Layers or Via Selective Etching and Filling of Voids. The techniques disclosed in this referenced application may be combined with the techniques and alternatives set forth explicitly herein to derive additional alternative embodiments. In particular, the structural features are still defined on a planar-layer-by-planar-layer basis but material associated with some layers are formed along with material for other layers such that interlacing of deposited material occurs. Such interlacing may lead to reduced structural distortion during formation or improved interlayer adhesion. This patent application is herein incorporated by reference as if set forth in full.

The patent applications and patents set forth below are hereby incorporated by reference herein as if set forth in full. The teachings in these incorporated applications can be combined with the teachings of the instant application in many ways: For example, enhanced methods of producing structures may be derived from some combinations of teachings, enhanced structures may be obtainable, enhanced apparatus may be derived, and the like.

| U.S. patent App No., Filing Date U.S. App Pub No., Pub Date U.S. Pat. No., Issue Date | Inventor, Title |
|---|---|
| 09/493,496 - Jan. 28, 2000 U.S. Pat. No. 6,790,377 - Sep. 14, 2004 | Cohen, "Method For Electrochemical Fabrication" |
| 10/677,556 - Oct. 1, 2003 2004-0134772 - Jul. 15, 2004 | Cohen, "Monolithic Structures Including Alignment and/or Retention Fixtures for Accepting Components" |
| 10/830,262 - Apr. 21, 2004 2004-0251142A - Dec. 16, 2004 U.S. Pat. No. 7,198,704 - Apr. 3, 2007 | Cohen, "Methods of Reducing Interlayer Discontinuities in Electrochemically Fabricated Three-Dimensional Structures" |
| 10/271,574 - Oct. 15, 2002 2003-0127336A - July 10, 2003 U.S. Pat. No. 7,288,178 - Oct. 30, 2007 | Cohen, "Methods of and Apparatus for Making High Aspect Ratio Microelectromechanical Structures" |
| 10/697,597 - Dec. 20, 2002 2004-0146650A - Jul. 29, 2004 | Lockard, "EFAB Methods and Apparatus Including Spray Metal or Powder Coating Processes" |
| 10/677,498 - Oct. 1, 2003 2004-0134788 - Jul. 15, 2004 U.S. Pat. No. 7,235,166 - Jun. 26, 2007 | Cohen, "Multi-cell Masks and Methods and Apparatus for Using Such Masks To Form Three-Dimensional Structures" |
| 10/724,513 - Nov. 26, 2003 2004-0174124 - Jul. 29, 2004 U.S. Pat. No. 7,368,044 - May 6, 2008 | Cohen, "Non-Conformable Masks and Methods and Apparatus for Forming Three-Dimensional Structures" |
| 10/607,931 - Jun. 27, 2003 2004-0140862 - Jul. 22, 2004 U.S. Pat. No. 7,239,219 - Jul. 3, 2007 | Brown, "Miniature RF and Microwave Components and Methods for Fabricating Such Components" |
| 10/841,100 - May 7, 2004 2005-0032362 - Feb. 10, 2005 U.S. Pat. No. 7,109,118 - Sep. 19, 2006 | Cohen, "Electrochemical Fabrication Methods Including Use of Surface Treatments to Reduce Overplating and/or Planarization During Formation of Multi-layer Three-Dimensional Structures" |
| 10/387,958 - Mar. 13, 2003 2003-022168A - Dec. 4, 2003 | Cohen, "Electrochemical Fabrication Method and Application for Producing Three-Dimensional Structures Having Improved Surface Finish" |
| 10/434,494 - May 7, 2003 2004-0000489A - Jan. 1, 2004 | Zhang, "Methods and Apparatus for Monitoring Deposition Quality During Conformable Contact Mask Plating Operations" |
| 10/434,289 - May 7, 2003 20040065555A - Apr. 8, 2004 | Zhang, "Conformable Contact Masking Methods and Apparatus Utilizing In Situ Cathodic Activation of a Substrate" |
| 10/434,294 - May 7, 2003 2004-0065550A - Apr. 8, 2004 | Zhang, "Electrochemical Fabrication Methods With Enhanced Post Deposition Processing Enhanced Post Deposition Processing" |
| 10/434,295 - May 7, 2003 2004-0004001A - Jan. 8, 2004 | Cohen, "Method of and Apparatus for Forming Three-Dimensional Structures Integral With Semiconductor Based Circuitry" |
| 10/434,315 - May 7, 2003 2003-0234179 A - Dec. 25, 2003 U.S. Pat. No. 7,229,542 - Jun. 12, 2007 | Bang, "Methods of and Apparatus for Molding Structures Using Sacrificial Metal Patterns" |
| 10/434,103 - May 7, 2004 2004-0020782A - Feb. 5, 2004 U.S. Pat. No. 7,160,429 - Jan. 9, 2007 | Cohen, "Electrochemically Fabricated Hermetically Sealed Microstructures and Methods of and Apparatus for Producing Such Structures" |
| 10/841,006 - May 7, 2004 2005-0067292 - May 31, 2005 | Thompson, "Electrochemically Fabricated Structures Having Dielectric or Active Bases and Methods of and Apparatus for Producing Such Structures" |
| 10/434,519 - May 7, 2003 2004-0007470A - Jan. 15, 2004 U.S. Pat. No. 7,252,861 - Aug. 7, 2007 | Smalley, "Methods of and Apparatus for Electrochemically Fabricating Structures Via Interlaced Layers or Via Selective Etching and Filling of Voids" |
| 10/724,515 - Nov. 26, 2003 2004-0182716 - Sep. 23, 2004 U.S. Pat. No. 7,291,254 - Nov. 6, 2007 | Cohen, "Method for Electrochemically Forming Structures Including Non-Parallel Mating of Contact Masks and Substrates" |
| 10/841,347 - May 7, 2004 2005-0072681 - Apr. 7, 2005 | Cohen, "Multi-step Release Method for Electrochemically Fabricated Structures" |
| 60/533,947 - Dec. 31, 2003 | Kumar, "Probe Arrays and Method for Making" |
| 60/534,183 - Dec. 31, 2003 | Cohen, "Method and Apparatus for Maintaining Parallelism of Layers and/or Achieving Desired Thicknesses of Layers During the Electrochemical Fabrication of Structures" |
| 11/733.195 - Apr. 9, 2007 2008-0050524 - Feb. 28, 2008 | Kumar, "Methods of Forming Three-Dimensional Structures Having Reduced Stress and/or Curvature" |
| 11/506,586 - Aug. 8, 2006 20007-0039828 - Feb. 22, 2007 | Cohen, "Mesoscale and Microscale Device Fabrication Methods Using Split Structures and Alignment Elements" |

-continued

| U.S. patent App No., Filing Date U.S. App Pub No., Pub Date U.S. Pat. No., Issue Date | Inventor, Title |
|---|---|
| 10/949,744 - Sep. 24, 2004 2005-0126916 - Jun. 16, 2005 | Lockard, "Three-Dimentional Structures Having Feature Sizes Smaller Than a Minimum Feature Size and Methods for Fabricating" |

Though various portions of this specification have been provided with headers, it is not intended that the headers be used to limit the application of teachings found in one portion of the specification from applying to other portions of the specification. For example, it should be understood that alternatives acknowledged in association with one embodiment, are intended to apply to all embodiments to the extent that the features of the different embodiments make such application functional and do not otherwise contradict or remove all benefits of the adopted embodiment. Various other embodiments of the present invention exist. Some of these embodiments may be based on a combination of the teachings herein with various teachings incorporated herein by reference.

In view of the teachings herein, many further embodiments, alternatives in design and uses of the embodiments of the instant invention will be apparent to those of skill in the art. As such, it is not intended that the invention be limited to the particular illustrative embodiments, alternatives, and uses described above but instead that it be solely limited by the claims presented hereafter.

We claim:

1. A surgical procedure for approximating tissue within a patient's body, comprising:
   (a) providing a control wire;
   (b) locating an approximation instrument within the body of a patient at the end of a catheter; the instrument comprising:
      (i) a first set of expandable elements;
      (ii) a second set of expandable elements;
      (iii) a rail along which the first and second sets of expandable elements are located; and
      (iv) a locking mechanism for allowing the first and second sets of expandable elements to be moved to more proximate positions while inhibiting movement of the first and second sets of expandable elements to a more distant relative position along a length of the rail, after being moved to the more proximate positions;
      (v) a threaded engagement feature for engaging the control wire;
      (vi) a seat region for engaging a push tube wherein the wire and the push tube engage relatively movable elements and that upon relative motion can be made to bring the first and second set of expandable elements to their more proximate positions;
      (vii) a controllable stop element that inhibits distal expansion wings, comprising a set of expandable elements selected from a group consisting of the (1) first set of expandable elements, and (2) the second set of expandable elements, from extending beyond a desired retention position when located in a first position and allows distal axial collapse of the distal expansion wings when located in another position so that the instrument may be extracted in its entirety from a proximal side of the tissue;
   (c) inserting a distal end of the instrument from the proximal side of the tissue through a proximal tissue region and then through a separated distal tissue region;
   (d) expanding the first set of expandable elements
   (e) locating the first set of expanded elements against a wall of the distal tissue region;
   (f) expanding the second set of expandable elements
   (g) locating the second set of expanded elements against a wall of the proximal tissue region;
   (h) relatively moving the first set of expanded elements and the second set of expanded elements toward one another to bring the proximal and distal tissue regions into a more proximate position; and
   (i) releasing at least a portion of the instrument from the catheter by rotating the control wire in a first direction so that a portion of instrument that contains the first and second sets of expanded elements remains in the body of the patient and retains the distal and proximal tissue regions in the more proximate position.

2. The procedure of claim 1 wherein the instrument is disengaged from the distal and proximal tissue regions by rotating a portion of the instrument in an opposite direction to that of the first direction to allow collapse of the distal expansion wings in a distal direction as the instrument is extracted in a proximal direction.

3. The procedure of claim 1 wherein the control wire is rotatable relative to the threaded engagement feature such that upon rotation in one direction the control wire is disengaged while rotation in an opposite direction causes the turning of an oppositely threaded screw which causes a movement of the stop to a second position.

4. The procedure of claim 1 wherein at least one of the first set of expandable elements or the second set of expandable elements comprise toggle wings that pivot open along at least one axis that is perpendicular to a longitudinal axis of the instrument.

5. The procedure of claim 4 wherein the toggle wings expand via a force induced by at least one spring located within the instrument.

6. The procedure of claim 4 wherein the other of the first set of expandable elements or the second set of expandable elements comprise toggle wings that pivot open along at least one axis that is perpendicular to a longitudinal axis of the instrument.

7. The procedure of claim 6 wherein the toggle wings of the other of the first set of expandable elements or the second set of expandable elements expand via a force induced by at least one spring located within the instrument.

* * * * *